(12) United States Patent
Day et al.

(10) Patent No.: US 11,080,367 B2
(45) Date of Patent: Aug. 3, 2021

(54) SYSTEM-WIDE PROBABILISTIC ALERTING AND ACTIVATION

(71) Applicant: General Electric Company, Schenectady, NY (US)

(72) Inventors: Andrew Day, Newtown, PA (US); Christopher Johnson, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 326 days.

(21) Appl. No.: 16/148,584

(22) Filed: Oct. 1, 2018

(65) Prior Publication Data
US 2019/0034579 A1 Jan. 31, 2019

Related U.S. Application Data

(63) Continuation of application No. 14/746,385, filed on Jun. 22, 2015, now Pat. No. 10,089,441.

(51) Int. Cl.
*G16H 40/20* (2018.01)
*G06F 19/00* (2018.01)

(52) U.S. Cl.
CPC ............ *G06F 19/00* (2013.01); *G16H 40/20* (2018.01)

(58) Field of Classification Search
CPC ..... G06Q 10/06; G06F 19/327; G06F 19/345; G06F 9/5011; G16H 40/00; G16H 40/20
See application file for complete search history.

(56) References Cited

U.S. PATENT DOCUMENTS

| 2006/0109961 A1* | 5/2006 | Mahesh ................. G06Q 50/22 379/93.25 |
| 2007/0067181 A1 | 3/2007 | Dellinger et al. |

(Continued)

FOREIGN PATENT DOCUMENTS

WO WO-2006093544 A2 * 9/2006 ............. G16H 80/00

OTHER PUBLICATIONS

United States Patent and Trademark Office, "Non-Final Office Action", issued in connection with U.S. Appl. No. 14/746,385, dated Dec. 21, 2017, 23 pages.

(Continued)

*Primary Examiner* — John A Pauls
(74) *Attorney, Agent, or Firm* — Hanley, Flight & Zimmerman, LLC

(57) ABSTRACT

Systems, methods, and computer program products that enable system-wide probabilistic forecasting, alerting, optimizing and activating resources in the delivery of care to address both immediate (near real-time) conditions as well as probabilistic forecasted operational states of the system over an interval that is selectable from the current time to minutes, hours and coming days or weeks ahead are provided. There are multiple probabilistic future states that are implemented in these different time intervals and these may be implemented concurrently for an instant in time control, near term, and long term. Those forecasts along with their optimized control of hospital capacity may be independently calculated and optimized, such as for a dynamic workflow direction over the next hour and also a patient's stay over a period of days. In the present application, a probabilistic and conditional workflow reasoning system enabling complex team-based decisions that improve capacity, satisfaction, and safety is provided. A means to consume user(s) judgment, implement control on specific resource assignments (Continued)

and tasks in a clinical workflow is enabled, as is the dynamical and optimal control of the other care delivery assets being managed by the system so as to more probably achieve operating criteria such as throughput, waiting and schedule risk.

20 Claims, 13 Drawing Sheets

(56) References Cited

U.S. PATENT DOCUMENTS

| | | | |
|---|---|---|---|
| 2009/0089092 A1* | 4/2009 | Johnson | G06F 19/00 705/2 |
| 2012/0065987 A1* | 3/2012 | Farooq | G16H 40/20 705/2 |
| 2013/0086590 A1 | 4/2013 | Morris et al. | |
| 2013/0132108 A1* | 5/2013 | Solilov | G06Q 50/22 705/2 |
| 2016/0371441 A1 | 12/2016 | Day et al. | |

OTHER PUBLICATIONS

United States Patent and Trademark Office, "Notice of Allowance and Fees Due", issued in connection with U.S. Appl. No. 14/746,385, dated May 18, 2018, 17 pages.

* cited by examiner

SYSTEM-WIDE PROBABILISTIC ALERTING AND ACTIVATION

RELATED APPLICATIONS

This patent arises from a continuation of U.S. patent application Ser. No. 14/746,385, entitled "SYSTEM-WIDE PROBABILISTIC ALERTING AND ACTIVATION", filed Jun. 22, 2015, which is incorporated herein by reference in its entirety.

FIELD OF DISCLOSURE

The present disclosure relates to healthcare operations, and more particularly to systems, methods and computer program products to provide system-wide probabilistic alerting and activation that automatically controls the resources and conditionally allocates capacity across departments to achieve a minimal wait state through an interval of time.

BACKGROUND

The statements in this section merely provide background information related to the disclosure and may not constitute prior art.

A need in hospital operations management is creating an operational control center which reconciles the needs of individual departments for the greater aims of more capacity at the institutional level. For these tradeoffs to be rationally made, the interdependencies of the millions of combinations of capacity, asset assignment, staff assignment and protocol choice must be calculated and then reduced to a small number of ranked and feasible scenarios so that an automated control may direct most operations and then isolate the collaboration of cross functional teams involved in managing the flow of patients and operations of the hospital with informed user intervention. These cross departmental decisions that benefit from analytical processing yet also need user judgment may be improved from the current practice of "huddles" where no probabilistic duration and little dynamic interdependencies can be considered. The byproduct of a lack of ability to forecast multiple feasible futures results in the current practice of scheduling "slack" into core operations practice. This slack is used as a physical time buffer to account for scheduling mismatching of patient services across departments when the departments do not have an ability to jointly co-optimize sequencing. These departments include functions such as admitting, bed management, scheduling, staffing, environmental systems, cleaning staff, transport dispatchers, diagnostic imaging, labs, physical therapy, meals and other related functions. Each of these functional members has access to their function-specific transactional IT systems and currently use them to perform their work. The present disclosure enables cross departmental operations automation and user intervention when needed.

In addition to their individual transactional systems, which may be their current departmental applications, tone function of the disclosed system supports these teams in effective collaboration by displaying key dashboards from select sub-systems onto large screen displays that are mounted on the walls in a conference room during an operations huddle, typically conducted once or twice a day or in an operations center which may be a dedicated room or virtual presence. Each of these source systems remain distinct and are often provided from multiple vendors. Users are left to determine the hundreds of interdependencies of a patient as the patient's care is planned and managed. Yet the actual co-optimization is impossible to reconcile with individual systems, especially when conditional branches or sequences are available in a care plan that traverses departments, as most do. Patients experience this lack of co-optimized control of assets and capacity as "hurry and wait". Those delays accumulate and restrict hospital throughput.

It should be noted that in a hospital environment it can be conservatively estimated that if there were. 250 rolling patients, 5 available pathways, 15 pathway steps, this results in a potential reorder of 360,360 possible combinations. Assuming it would take someone 30 seconds to run one combination, it would take 20,568 person years to choose the correct combination. Being infeasible, the tradition is to create rules of thumb or standard policies that build in slack or margin of operational error.

BRIEF SUMMARY

In view of the above, there is a need for a hospital control system that estimates task durations, reconciles resource interdependencies and automatically finds the optimal sequence and assignment of assets and resources for many patients across multiple departments through a forecast interval. The disclosed systems, methods, and computer program products perform system-wide probabilistic alerting and activation. The above-mentioned needs are addressed by the subject matter described herein and will be understood in the following specification.

According to one aspect of the present disclosure, a system that allows system-wide probabilistic alerting and operations control activation is provided.

According to another aspect of the present disclosure, a method that allows system-wide probabilistic forecasting, alerting, optimization and activation is provided.

This summary briefly describes aspects of the subject matter described below in the Detailed Description, and is not intended to be used to limit the scope of the subject matter described in the present disclosure.

BRIEF DESCRIPTION OF THE DRAWINGS

The features and technical aspects of the system and method disclosed herein will become apparent in the following Detailed Description set forth below when taken in conjunction with the drawings in which like reference numerals indicate identical or functionally similar elements.

DETAILED DESCRIPTION

Figure 1:
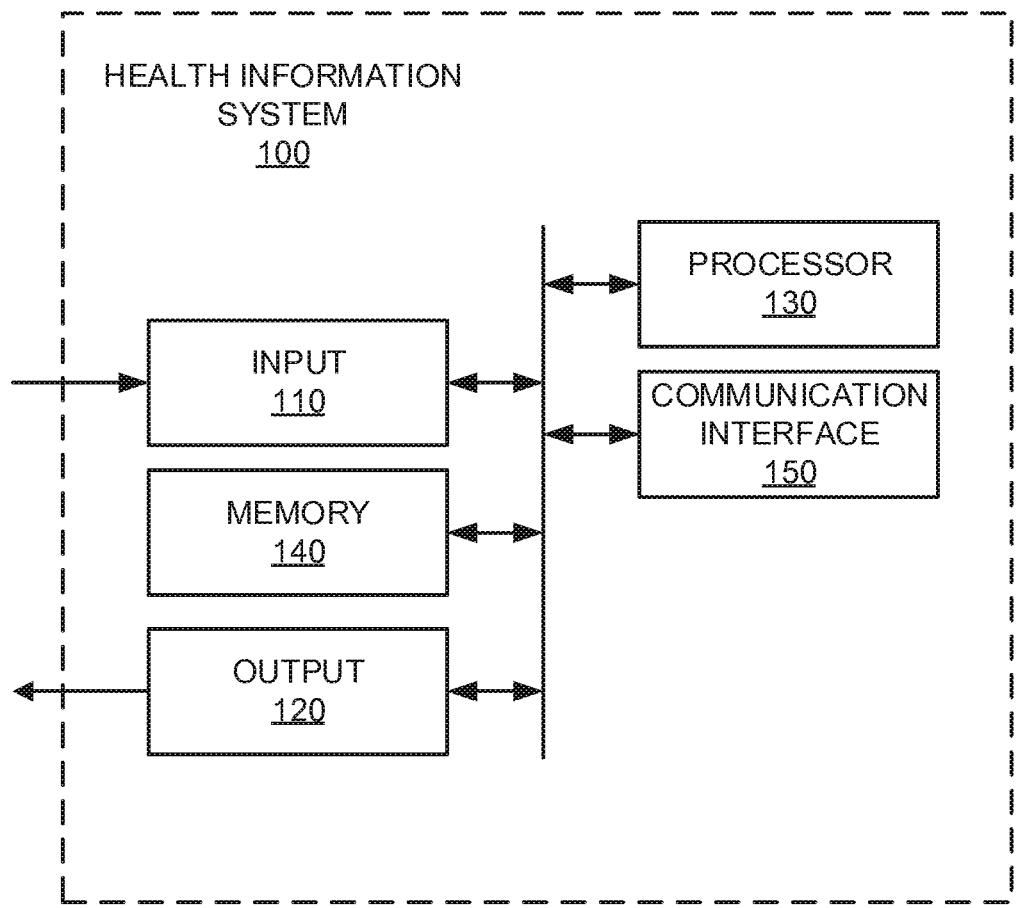
FIG. 1 shows a block diagram of an example healthcare-focused information system.

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized and that logical, mechanical, electrical and other changes may be made without departing from the scope of the subject matter of this disclosure. The following detailed description is, therefore, provided to describe an exemplary implementation and not to be taken as limiting on the scope of the subject matter described in this disclosure. Certain features from different aspects of the following description may be combined to form yet new aspects of the subject matter discussed below.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements.

I. Overview

Aspects disclosed and described herein enable system-wide probabilistic alerting and activation to address both immediate (near real-time) conditions as well as probabilistic forecasted operational states of the system over an interval that is selectable from the current time to minutes, hours and coining days or weeks ahead. There are multiple probabilistic future states that are implemented in these different time intervals and these may be implemented concurrently for an instant in time control, near term, and long term. Those forecasts along with their optimized control of hospital capacity may be independently calculated and optimized, such as for a dynamic workflow direction over the next hour and also a patient's stay over a period of days. In the present application, a probabilistic and conditional workflow reasoning system enabling complex team based decisions that improve capacity, satisfaction, and safety is considered.

Other aspects, such as those discussed in the following and others as can be appreciated by one having ordinary skill in the art upon reading the enclosed description, are also possible.

II. Example Operating Environment

Health information, also referred to as healthcare information and/or healthcare data, relates to information generated and/or used by a healthcare entity. Health information can be information associated with health of one or more patients, for example. Health information may include protected health information (PHI), as outlined in the Health Insurance Portability and Accountability Act (HIPAA), which is identifiable as associated with a particular patient and is protected from unauthorized disclosure. Health information can be organized as internal information and external information. Internal information includes patient encounter information (e.g., patient-specific data, aggregate data, comparative data, etc.) and general healthcare operations information, etc. External information includes comparative data, expert and/or knowledge-based data, etc. Information can have both a clinical (e.g., diagnosis, treatment, prevention, etc.) and administrative (e.g., scheduling, billing, management, etc.) purpose.

Institutions, such as healthcare institutions, having complex network support environments and sometimes chaotically driven process flows utilize secure handling and safeguarding of the flow of sensitive information (e.g., personal privacy). A need for secure handling and safeguarding of information increases as a demand for flexibility, volume, and speed of exchange of such information grows. For example, healthcare institutions provide enhanced control and safeguarding of the exchange and storage of sensitive patient PHI and employee information between diverse locations to improve hospital operational efficiency in an operational environment typically having a chaotic-driven demand by patients for hospital services. In certain examples, patient identifying information can be masked or even stripped from certain data depending upon where the data is stored and who has access to that data. In some examples, PHI that has been "de-identified" can be re-identified based on a key and/or other encoder/decoder.

A healthcare information technology infrastructure can be adapted to service multiple business interests while providing clinical information and services. Such an infrastructure may include a centralized capability including, for example, a data repository, reporting, discreet data exchange/connectivity, "smart" algorithms, personalization/consumer decision support, etc. This centralized capability provides information and functionality to a plurality of users including medical devices, electronic records, access portals, pay for performance (P4P), chronic disease models, and clinical health information exchange/regional health information organization (HIE/RHIO), and/or enterprise pharmaceutical studies, home health, for example.

Interconnection of multiple data sources helps enable an engagement of all relevant members of a patient's care team and helps improve an administrative and management burden on the patient for managing his or her care. Particularly, interconnecting the patient's electronic medical record and/or other medical data can help improve patient care and management of patient information. Furthermore, patient care compliance is facilitated by providing tools that automatically adapt to the specific and changing health conditions of the patient and provide comprehensive education and compliance tools to drive positive health outcomes.

In certain examples, healthcare information can be distributed among multiple applications using a variety of database and storage technologies and data formats. To provide a common interface and access to data residing across these applications, a connectivity framework (CF) can be provided which leverages common data and service models (CDM and CSM) and service oriented technologies, such as an enterprise service bus (ESB) to provide access to the data.

In certain examples, a variety of user interface frameworks and technologies can be used to build applications for health information systems including, but not limited to, MICROSOFT® ASP.NET, AJAX®, MICROSOFT® Windows Presentation Foundation, GOGGLE® Web Toolkit, MICROSOFT® Silverlight, ADOBE®, and others. Applications can be composed from libraries of information widgets to display multi-content and multi-media information, for example. In addition, the framework enables users to tailor layout of applications and interact with underlying data.

In certain examples, an advanced Service-Oriented Architecture (SOA) with a modern technology stack helps provide robust interoperability, reliability, and performance. Example SOA includes a three-fold interoperability strategy including a central repository (e.g., a central repository built from Health Level Seven (HL7) transactions), services for working in federated environments, and visual integration with third-party applications. Certain examples provide portable content enabling plug 'n play content exchange among healthcare organizations. A standardized vocabulary using common standards (e.g., LOINC, SNOMED CT, RxNorm, FDB, ICD-9, ICD-10, etc.) is used for interoperability, for example. Certain examples provide an intuitive user interface to help minimize end-user training. Certain examples facilitate user-initiated launching of third-party applications directly from a desktop interface to help provide a seamless workflow by sharing user, patient, and/or other contexts. Certain examples provide real-time (or at least substantially real time assuming some system delay) patient data from one or more information technology (IT) systems and facilitate comparison(s) against evidence-based best practices. Certain examples provide one or more dashboards for specific sets of patients. Dashboard(s) can be based on condition, role, and/or other criteria to indicate variation(s) from a desired practice, for example.

A. Example Healthcare Information System

An information system can be defined as an arrangement of information/data, processes, and information technology that interact to collect, process, store, and provide informational output to support delivery of healthcare to one or more patients. Information technology includes computer technology (e.g., hardware and software) along with data and telecommunications technology (e.g., data, image, and/or voice network, etc.).

Turning now to the figures, FIG. 1 shows a block diagram of an example healthcare-focused information system 100. Example system 100 can be configured to implement a variety of systems and processes including image storage (e.g., picture archiving and communication system (PACS), etc.), image processing and/or analysis, radiology reporting and/or review (e.g., radiology information system (RIS), etc.), computerized provider order entry (CPOE) system, clinical decision support, patient monitoring, population health management (e.g., population health management system (PHMS), health information exchange (HIE), etc.), healthcare data analytics, cloud-based image sharing, electronic medical record (e.g., electronic medical record system (EMR), electronic health record system (EHR), electronic patient record (EPR), personal health record system (PHR), etc.), and/or other health information system (e.g., clinical information system (CIS), hospital information system (HIS), patient data management system (PDMS), laboratory information system (LIS), cardiovascular information system (CVIS), etc.

As illustrated in FIG. 1, the example information system 100 includes an input 110, an output 120, a processor 130, a memory 140, and a communication interface 150. The components of example system 100 can be integrated in one device or distributed over two or more devices.

Example input 110 may include a keyboard, a touch-screen, a mouse, a trackball, a track pad, optical barcode recognition, voice command, etc. or combination thereof used to communicate an instruction or data to system 100. Example input 110 may include an interface between systems, between user(s) and system 100, etc.

Example output 120 can provide a display generated by processor 130 for visual illustration on a monitor or the like. The display can be in the form of a network interface or graphic user interface (GUI) to exchange data, instructions, or illustrations on a computing device via communication interface 150, for example. Example output 120 may include a monitor (e.g., liquid crystal display (LCD), plasma display, cathode ray tube (CRT), etc.), light emitting diodes (LEDs), a touch-screen, a printer, a speaker, or other conventional display device or combination thereof.

Example processor 130 includes hardware and/or software configuring the hardware to execute one or more tasks and/or implement a particular system configuration. Example processor 130 processes data received at input 110 and generates a result that can be provided to one or more of output 120, memory 140, and communication interface 150. For example, example processor 130 can take user annotation provided via input 110 with respect to an image displayed via output 120 and can generate a report associated with the image based on the annotation. As another example, processor 130 can process updated patient information obtained via input 110 to provide an updated patient record to an EMR via communication interface 150.

Example memory 140 may include a relational database, an object-oriented database, a data dictionary, a clinical data repository, a data warehouse, a data mart, a vendor neutral archive, an enterprise archive, etc. Example memory 140 stores images, patient data, best practices, clinical knowledge, analytics, reports, etc. Example memory 140 can store data and/or instructions for access by the processor 130. In certain examples, memory 140 can be accessible by an external system via the communication interface 150.

In certain examples, memory 140 stores and controls access to encrypted information, such as patient records, encrypted update-transactions for patient medical records, including usage history, etc. In an example, medical records can be stored without using logic structures specific to medical records. In such a manner, memory 140 is not searchable. For example, a patient's data can be encrypted with a unique patient-owned key at the source of the data. The data is then uploaded to memory 140. Memory 140 does not process or store unencrypted data thus minimizing privacy concerns. The patient's data can be downloaded and decrypted locally with the encryption key.

For example, memory 140 can be structured according to provider, patient, patient/provider association, and document. Provider information may include, for example, an identifier, a name, and address, a public key, and one or more security categories. Patient information may include, for example, an identifier, a password hash, and an encrypted email address. Patient/provider association information may include a provider identifier, a patient identifier, an encrypted key, and one or more override security categories. Document information may include an identifier, a patient identifier, a clinic identifier, a security category, and encrypted data, for example.

Example communication interface 150 facilitates transmission of electronic data within and/or among one or more systems. Communication via communication interface 150 can be implemented using one or more protocols. In some examples, communication via communication interface 150 occurs according to one or more standards (e.g., Digital Imaging and Communications in Medicine (DICOM), Health Level Seven (HL7), ANSI X12N, etc.). Example communication interface 150 can be a wired interface (e.g., a data bus, a Universal Serial Bus (USB) connection, etc.) and/or a wireless interface (e.g., radio frequency, infrared, near field communication (NFC), etc.). For example, communication interface 150 may communicate via wired local area network (LAN), wireless LAN, wide area network (WAN), etc. using any past, present, or future communication protocol (e.g., BLUETOOTH™, USB 2.0, USB 3.0, etc.).

In certain examples, a Web-based portal may be used to facilitate access to information, patient care and/or practice management, etc. Information and/or functionality available via the Web-based portal may include one or more of order entry, laboratory test results review system, patient information, clinical decision support, medication management, scheduling, electronic mail and/or messaging, medical resources, etc. In certain examples, a browser-based interface can serve as a zero footprint, zero download, and/or other universal viewer for a client device.

In certain examples, the Web-based portal serves as a central interface to access information and applications, for example. Data may be viewed through the Web-based portal or viewer, for example. Additionally, data may be manipulated and propagated using the Web-based portal, for example. Data may be generated, modified, stored and/or used and then communicated to another application or system to be modified, stored and/or used, for example, via the Web-based portal, for example.

The Web-based portal may be accessible locally (e.g., in an office) and/or remotely (e.g., via the Internet and/or other private network or connection), for example. The Web-based portal may be configured to help or guide a user in accessing data and/or functions to facilitate patient care and practice management, for example. In certain examples, the Web-based portal may be configured according to certain rules, preferences and/or functions, for example. For example, a user may customize the Web portal according to particular desires, preferences and/or requirements.

B. Example Healthcare Infrastructure

Figure 2:
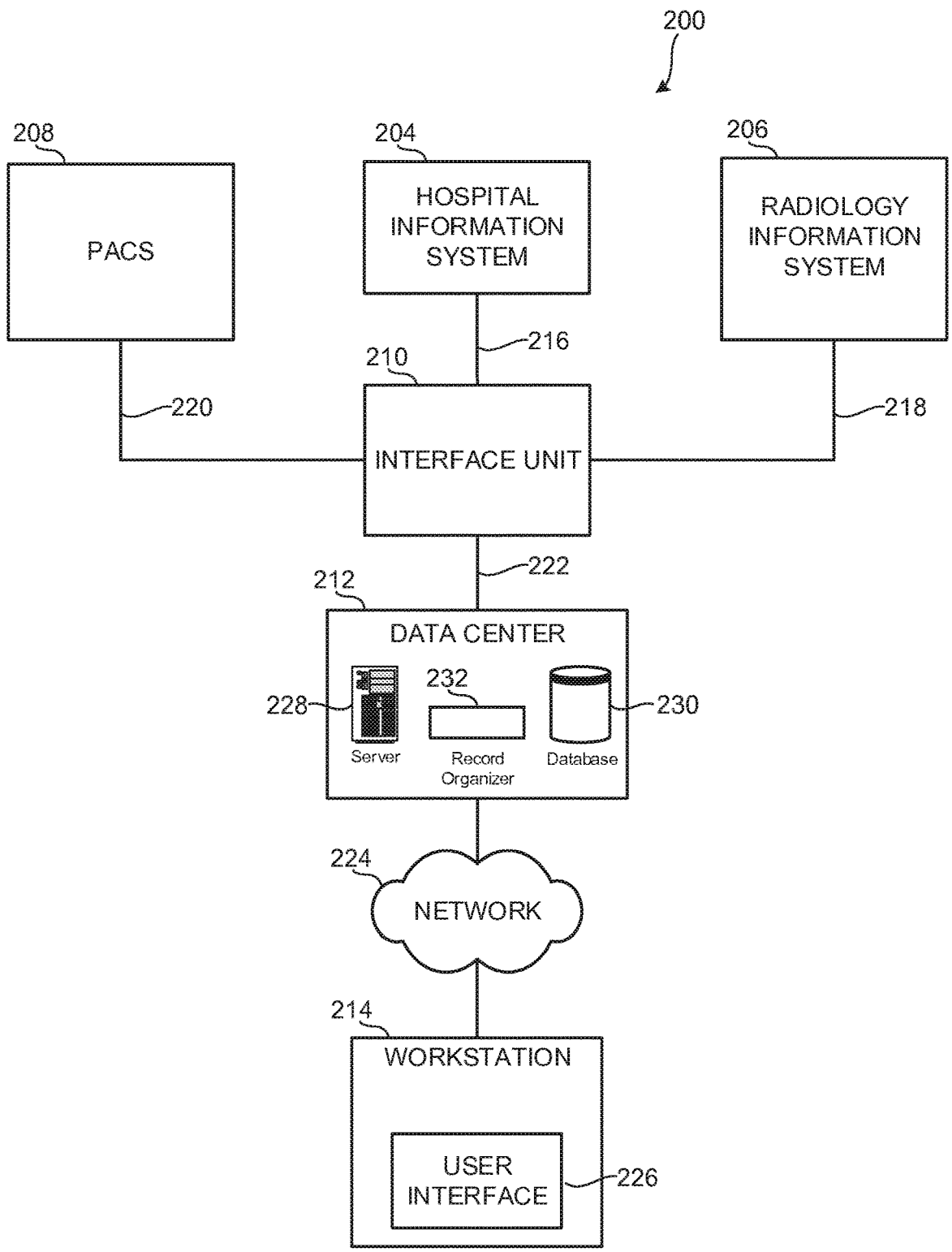
FIG. 2 shows a block diagram of an example healthcare information infrastructure including one or more systems.

FIG. 2 shows a block diagram of an example healthcare information infrastructure 200 including one or more subsystems such as the example healthcare-related information system 100 illustrated in FIG. 1. Example healthcare system 200 includes a HIS 204, a RIS 206, a PACS 208, an interface unit 210, a data center 212, and a workstation 214. In the illustrated example, HIS 204, RIS 206, and PACS 208 are housed in a healthcare facility and locally archived. However, in other implementations, HIS 204, RIS 206, and/or PACS 208 may be housed within one or more other suitable locations. In certain implementations, one or more of PACS 208, RIS 206, HIS 204, etc., may be implemented remotely via a thin client and/or downloadable software solution. Furthermore, one or more components of the healthcare system 200 can be combined and/or implemented together. For example, RIS 206 and/or PACS 208 can be integrated with HIS 204; PACS 208 can be integrated with RIS 206; and/or the three example information systems 204, 206, and/or 208 can be integrated together. In other example implementations, healthcare system 200 includes a subset of the illustrated information systems 204, 206, and/or 208. For example, healthcare system 200 may include only one or two of HIS 204, RIS 206, and/or PACS 208. Information (e.g., scheduling, test results, exam image data, observations, diagnosis, etc.) can be entered into HIS 204, RIS 206, and/or PACS 208 by healthcare practitioners (e.g., radiologists, physicians, and/or technicians) and/or administrators before and/or after patient examination.

The HIS 204 stores medical information such as clinical reports, patient information, and/or administrative information received from, for example, personnel at a hospital, clinic, and/or a physician's office (e.g., an EMR, EHR, PHR, etc.). RIS 206 stores information such as, for example, radiology reports, radiology exam image data, messages, warnings, alerts, patient scheduling information, patient demographic data, patient tracking information, and/or physician and patient status monitors. Additionally, RIS 206 enables exam order entry (e.g., ordering an x-ray of a patient) and image and film tracking (e.g., tracking identities of one or more people that have checked out a film). In some examples, information in RIS 206 is formatted according to the HL-7 (Health Level Seven) clinical communication protocol. In certain examples, a medical exam distributor is located in RIS 206 to facilitate distribution of radiology exams to a radiologist workload for review and management of the exam distribution by, for example, an administrator.

PACS 208 stores medical images (e.g., x-rays, scans, three-dimensional renderings, etc.) as, for example, digital images in a database or registry. In some examples, the medical images are stored in PACS 208 using the Digital Imaging and Communications in Medicine (DICOM) format. Images are stored in PACS 208 by healthcare practitioners (e.g., imaging technicians, physicians, radiologists) after a medical imaging of a patient and/or are automatically transmitted from medical imaging devices to PACS 208 for storage. In some examples, PACS 208 can also include a display device and/or viewing workstation to enable a healthcare practitioner or provider to communicate with PACS 208.

The interface unit 210 includes a hospital information system interface connection 216, a radiology information system interface connection 218, a PACS interface connection 220, and a data center interface connection 222. Interface unit 210 facilities communication among HIS 204, RIS 206, PACS 208, and/or data center 212. Interface connections 216, 218, 220, and 222 can be implemented by, for example, a Wide Area Network (WAN) such as a private network or the Internet. Accordingly, interface unit 210 includes one or more communication components such as, for example, an Ethernet device, an asynchronous transfer mode (ATM) device, an 802.11 device, a DSL modem, a cable modem, a cellular modem, etc. In turn, the data center 212 communicates with workstation 214, via a network 224, implemented at a plurality of locations (e.g., a hospital, clinic, doctor's office, other medical office, or terminal, etc.). Network 224 is implemented by, for example, the Internet, an intranet, a private network, a wired or wireless Local Area Network, and/or a wired or wireless Wide Area Network. In some examples, interface unit 210 also includes a broker (e.g., a Mitra Imaging's PACS Broker) to allow medical information and medical images to be transmitted together and stored together.

Interface unit 210 receives images, medical reports, administrative information, exam workload distribution information, and/or other clinical information from the information systems 204, 206, 208 via the interface connections 216, 218, 220. If necessary (e.g., when different formats of the received information are incompatible), interface unit 210 translates or reformats (e.g., into Structured Query Language ("SQL") or standard text) the medical information, such as medical reports, to be properly stored at data center 212. The reformatted medical information can be transmitted using a transmission protocol to enable different medical information to share common identification elements, such as a patient name or social security number. Next, interface unit 210 transmits the medical information to data center 212 via data center interface connection 222. Finally, medical information is stored in data center 212 in, for example, the DICOM format, which enables medical images and corresponding medical information to be transmitted and stored together.

The medical information is later viewable and easily retrievable at workstation 214 (e.g., by their common identification element, such as a patient name or record number). Workstation 214 can be any equipment (e.g., a personal computer) capable of executing software that permits electronic data (e.g., medical reports) and/or electronic medical images (e.g., x-rays, ultrasounds, MRI scans, etc.) to be acquired, stored, or transmitted for viewing and operation. Workstation 214 receives commands and/or other input from a user via, for example, a keyboard, mouse, track ball, microphone, etc. Workstation 214 is capable of implementing a user interface 226 to enable a healthcare practitioner and/or administrator to interact with healthcare system 200. For example, in response to a request from a physician, user interface 226 presents a patient medical history. In other examples, a radiologist is able to retrieve and manage a workload of exams distributed for review to the radiologist via user interface 226. In further examples, an administrator reviews radiologist workloads, exam allocation, and/or operational statistics associated with the distribution of exams via user interface 226, In some examples, the administrator adjusts one or more settings or outcomes via user interface 226.

Example data center 212 of FIG. 2 is an archive to store information such as images, data, medical reports, and/or, more generally, patient medical records. In addition, data center 212 can also serve as a central conduit to information located at other sources such as, for example, local archives, hospital information systems/radiology information systems (e.g., HIS 204 and/or RIS 206), or medical imaging/storage systems (e.g., PACS 208 and/or connected imaging modalities). That is, the data center 212 can store links or indicators (e.g., identification numbers, patient names, or record numbers) to information. In the illustrated example, data center 212 is managed by an application server provider (ASP) and is located in a centralized location that can be accessed by a plurality of systems and facilities (e.g., hospitals, clinics, doctor's offices, other medical offices, and/or terminals). In some examples, data center 212 can be spatially distant from HIS 204, RIS 206, and/or PACS 208.

Example data center 212 of FIG. 2 includes a server 228, a database 230, and a record organizer 232. Server 228 receives, processes, and conveys information to and from the components of healthcare system 200. Database 230 stores the medical information described herein and provides access thereto. Example record organizer 232 of FIG. 2 manages patient medical histories, for example. Record organizer 232 can also assist in procedure scheduling, for example.

Certain examples can be implemented as cloud-based clinical information systems and associated methods of use. An example cloud-based clinical information system enables healthcare entities (e.g., patients, clinicians, sites, groups, communities, and/or other entities) to share information via web-based applications, cloud storage and cloud services. For example, the cloud-based clinical information system may enable a first clinician to securely upload information into the cloud-based clinical information system to allow a second clinician to view and/or download the information via a web application. Thus, for example, the first clinician may upload an x-ray image into the cloud-based clinical information system, and the second clinician may view the x-ray image via a web browser and/or download the x-ray image onto a local information system employed by the second clinician.

In certain examples, users (e.g., a patient and/or care provider) can access functionality provided by system 200 via a software-as-a-service (SaaS) implementation over a cloud or other computer network, for example. In certain examples, all or part of system 200 can also be provided via platform as a service (PaaS), infrastructure as a service (IaaS), etc. For example, system 200 can be implemented as a cloud-delivered Mobile Computing Integration Platform as a Service. A set of consumer-facing Web-based, mobile, and/or other applications enable users to interact with the PaaS, for example.

C. Example Methods of Use

Clinical workflows are typically defined to include one or more steps or actions to be taken in response to one or more events and/or according to a schedule. Events may include receiving a healthcare message associated with one or more aspects of a clinical record, opening a record(s) for new patient(s), receiving a transferred patient, reviewing and reporting on an image, and/or any other instance and/or situation that requires or dictates responsive action or processing. The actions or steps of a clinical workflow may include placing an order for one or more clinical tests, scheduling a procedure, requesting certain information to supplement a received healthcare record, retrieving additional information associated with a patient, providing instructions to a patient and/or a healthcare practitioner associated with the treatment of the patient, radiology image reading, and/or any other action useful in processing healthcare information. The defined clinical workflows may include manual actions or steps to be taken by, for example, an administrator or practitioner, electronic actions or steps to be taken by a system or device, and/or a combination of manual and electronic action(s) or step(s). While one entity of a healthcare enterprise may define a clinical workflow for a certain event in a first manner, a second entity of the healthcare enterprise may define a clinical workflow of that event in a second, different manner. In other words, different healthcare entities may treat or respond to the same event or circumstance in different fashions. Differences in workflow approaches may arise from varying preferences, capabilities, requirements or obligations, standards, protocols, etc. among the different healthcare entities.

In certain examples, a medical exam conducted on a patient can involve review b a healthcare practitioner, such as a radiologist, to obtain, for example, diagnostic information from the exam. In a hospital setting, medical exams can be ordered for a plurality of patients, all of which require review by an examining practitioner. Each exam has associated attributes, such as a modality, a part of the human body under exam, and/or an exam priority level related to a patient criticality level. Hospital administrators, in managing distribution of exams for review by practitioners, can consider the exam attributes as well as staff availability, staff credentials, and/or institutional factors such as service level agreements and/or overhead costs.

Additional workflows can be facilitated such as bill processing, revenue cycle mgmt., population health management, patient identity, consent management, etc.

III. Example System

Figure 3:
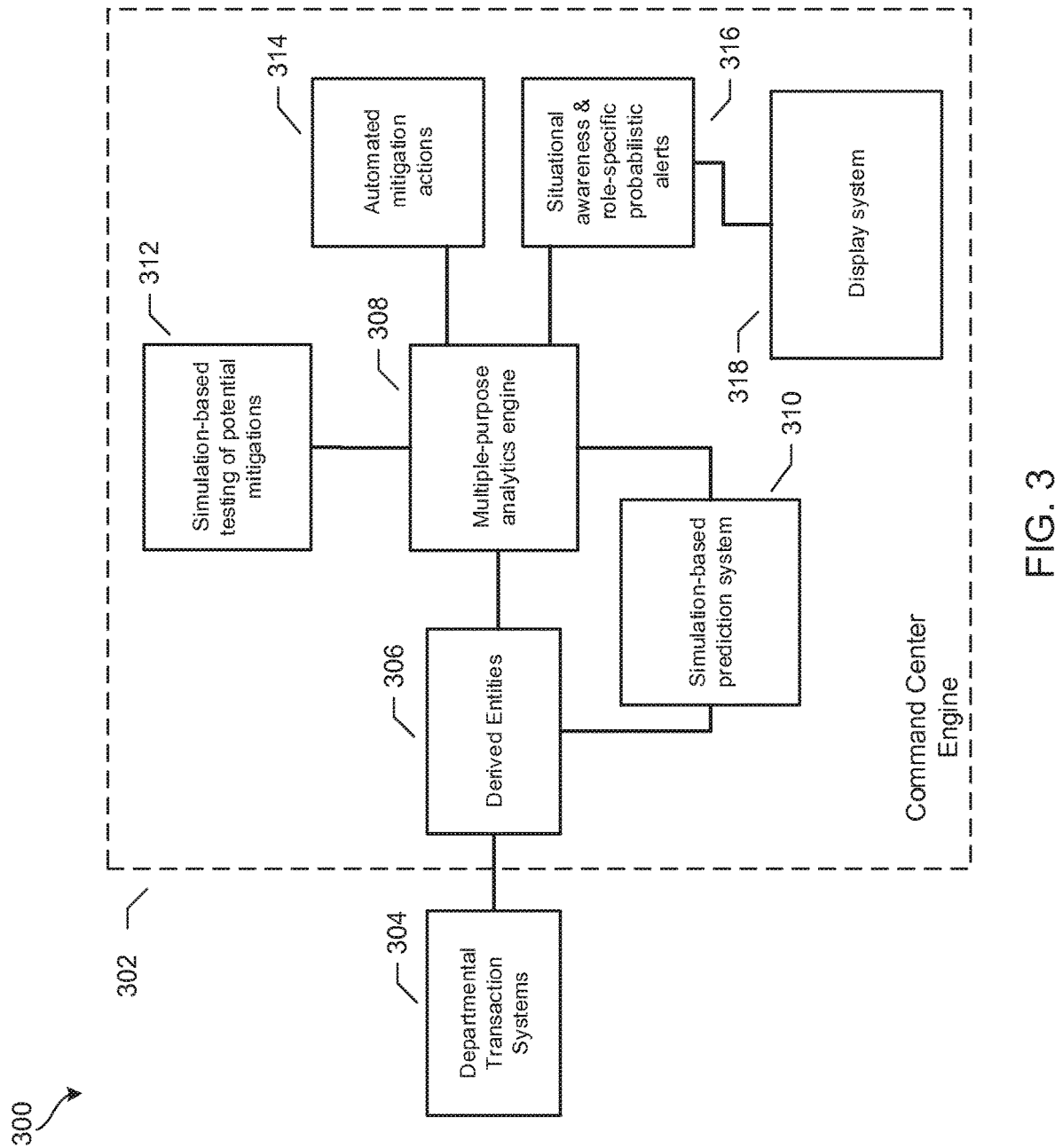
FIG. 3 is a block diagram illustrating an example cross-system probabilistic alerting and activation system, according to the present disclosure.

FIG. 3 depicts an example control system 300 for probabilistic cross-system forecasting, alerting, optimization and either automatic or user activation, according to one aspect of the present disclosure. System 300 includes a command center engine 302, which facilitates the collaboration of cross functional teams using data from department-wide systems to manage the hospital operations. Certain aspects include functions such as admitting, bed management, scheduling, staffing, environmental systems, transport dispatchers and other related functions, for example.

In certain aspects, command center engine 302 has the ability to parse data from multiple departmental transactional systems 304. A multitude of hospital transactional systems are interfaced via various methods. For example, a real-time HL7 message broker for patient-related information and via an enterprise service bus for system data information. Data received from these systems is parsed, transformed and integrated into the form of derived entity structures 306 in data injection servers. In certain aspects, the derived entities and the raw data is persisted in database servers. These derived entities 306 are queried by multiple-purpose analytics engine 308 and also provide input to a simulation-based prediction system 310. Simulation-based prediction system 310 provides probabilistic forecasts to multiple-purpose analytics engine 308. The near real-time and forecasted information is used by multiple-purpose analytics engine 308 to generate information about the operational state of the hospital operations, Multiple-purpose engine 308 provides automated mitigation actions 314 to other hospital systems and personnel and also provides situational awareness and role-specific probabilistic warning and alert states 316. In certain aspects, information is provided to users in command center engine 302 and elsewhere in the hospital system in the form of analytic tiles. Probabilistic alert information is used to take distinctive actions, based on rules, to mitigate defects and constraints automatically detected by the system.

As an example, command center engine 302 can use cross-system data, forecasts and probabilistic alerts to automatically and optimally control patient discharge and environmental services activity to better serve patients and improve hospital operational performance, such as reducing waiting delays for procedures and accelerating discharges. Data is extracted from multiple disparate systems 304, which for this example may include perioperative/procedural, DI, labs, therapy, transfer center, emergency department (ED), bed management and admitting. After being parsed, transformed, and integrated into derived entities 306, calculations are performed by multiple-purpose analytics engine 308 and simulation-based hospital operations prediction system 310 to identify states that indicate how patient flow is currently occurring or will occur in the forecasted future. The calculated defect states include when threshold time intervals are exceeded for conditions such as and not limited to: 1) patients holding in the OR when another case is scheduled to follow; 2) patients who are boarding in ED awaiting an inpatient bed that matches their needs; 3) patients who are queued in the transfer center to be transferred to the hospital from another care facility to provide a higher level of care; 4) patients who are waiting in admissions because their physician said they needed to be admitted; 5) patients who are dwelling PACU after having been medically cleared to proceed to the next level of care; 6) patients waiting for therapy, imaging and discharge. These defect states are calculated in real-time but are also projected over a forecast interval such as, for example, the next 48 hours using inferences, probabilistic calculations and the results of the simulation-based hospital operations prediction system 310. In this example, defect states that are determined to be urgent are set with a configurable threshold and trigger the following events, as examples, in the current time and/or the simulated forward future: 1) determine the hospital beds that are unoccupied and thus need to be cleaned; 2) match the unit the bed resides with the clinical specialty of the patient in need; 3) determine if the bed is the correct level of care for the patient (i.e., ICU vs. step down vs. acute, for example); 4) put this bed on a list to be cleaned immediately and alert the bed management team and the dispatcher for environmental services team of the urgent defect and suggested mitigation. Simultaneously, for each patient in the system with a status of Pending Discharge and for each patient identified by command center engine 302 as a potential discharge (for example, by examining derived entities 306 to determine if nursing or case management records suggest a patient meets clinical criteria for being a discharge candidate using probabilistic methods) determine if a bed in which the discharge candidate patient resides matches the clinical discipline (specialty) of the patient in need and if the bed the discharge candidate patient resides is the correct level of care for the patient in need. When these conditions are identified, the discharge candidate patient is accelerated for discharge activities and alerts are provided to the bed management team, case management, and clinical team on the unit of the urgent defect and suggested mitigation. The defects states and suggested mitigation are communicated via several methods including on a "priority discharge tile" in display system 318 in command center engine 302.

Figure 4:
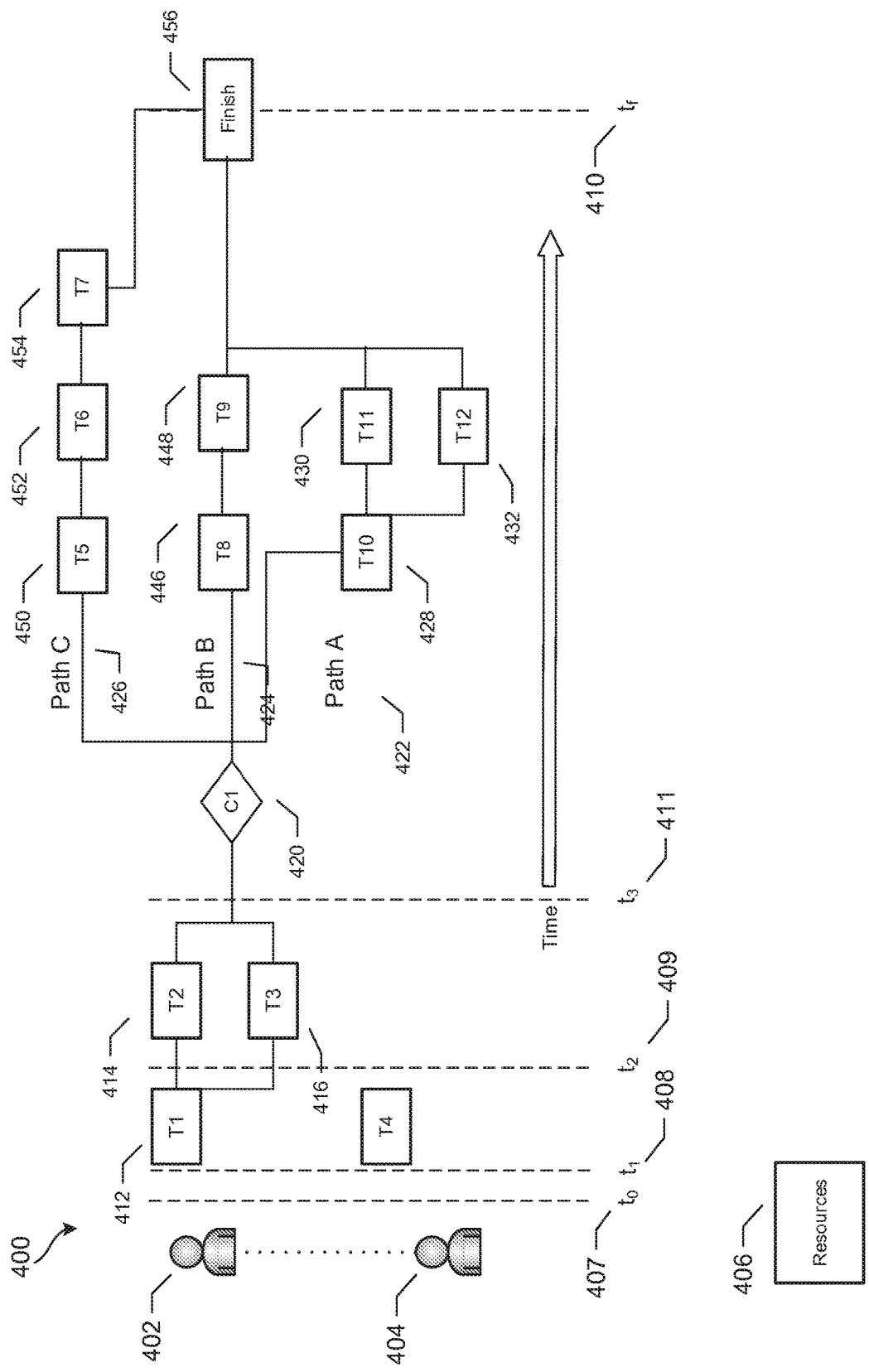
FIG. 4 shows a flow diagram illustrating an example method of operating the system of FIG. 3, according to the present disclosure.

A detail of the hospital operations control system is illustrated in FIG. 4, the example system 400 details the method of dynamically optimizing the hospital for the patients who are present and scheduled for their care delivery and for optimal recovery of the resource and patient schedule when an intervention is made, such as a manual assignment decision. The present system receives a preferred throughput and schedule risk, as input, from hospital administrators and controls the system to achieve those objectives to the fullest feasible extent. Controllable resources and controllable paths of sequences are defined as resources and paths of sequences that are able to be directly controlled. This is differentiated from those tasks, paths and resources which cannot be controlled (non-controllable).

For example, one patient 402 presents to the hospital by way of a scheduled arrival or an Emergency Department entry. The patient is triaged and provided a care plan which is an ordered sequence of tasks 412, 414, 416, 418, 428, 430, 432, 446, 448 that use and consume resources provided by the healthcare delivery system. The arrangement of these tasks may be changed at a conditional branch 420 that is controlled by the optimization logic, which is configured to be goal seeking of designated criteria, in order to achieve the satisfaction of the care plan at a desired criteria objective such as minimal time, illustrated as the time difference between 456 and 407, or highest probability of completing the plan by a point certain in future time 410 or a combination of cycle time, throughput or time variance.

Other patients 404 exist in the healthcare enterprise being controlled. These patients may already be admitted and actively managed and/or they may be future arrivals such as those who are scheduled for a clinical procedure, and/or they may be a randomized forecasted arrival sequence of hypothetical patients with attributes that may be adjusted by the system to mimic a typical historical patient mix or a specific concentration. The delivery of care by virtue of controlling the resources required 406 in the care plans of patients, is provided to the entire cohort of patients 402, 404 or any subset of the combined population at one or multiple time intervals in any combination of duration between times 407, 408, 409, 411, 110.

The resources 406 required for care are controlled by the system 400. Examples of resources that the tasks of a care protocol requires include care providers such as doctors, nurses, technicians; physical spaces such as patient rooms, beds, operating rooms, diagnostic imaging suites and lab space; and devices such as clinical apparatus or consumables. The locations of activities may be in one or more departments of a hospital, located in a single connected building, a campus or multiple facilities such as affiliated clinics and a patient's monitored home location. These resources 406 may have assignment limitations such as mutual exclusivity of use—for example, one patient in an operating room, or limits on the resource to multi-task, for example, a certain number of patients a nurse can care for. These constraints limit the assignment of resources to patients and thus act to limit the feasibility of executing a task that requires one or more of the resources. The disclosed system uses these limited resources as a control point in that by assigning resources to tasks, care is delivered. By not assigning a resource, patients are not able to proceed through a certain task(s). One or more patients are affected by limited resources. The disclosed system is managing the one or more patients concurrently with respect to the resource assignments and thus all combinations, which would overwhelm human decision making, are computed of patients, care plan tasks, resource assignments concurrently. Local and global optimal control, given the patients, their care plans and resources is achieved.

In one aspect, a number of objectives are being controlled for. For example, one or more patient throughput for an interval of time and the probability 606 (FIG. 6) that one or more patients will traverse the care plan by a certain time point, say final time ($t_f$) 410. Further, that there is a preference by the health system's management for the relationship between throughput and schedule risk. The sequences of tasks in a care plan may be configured to be conditional 420 so that the order or sequence may be switched, as a function of all the other system constraints, at one or more points in time. In an illustrative example, a given conditional branch 420 may have three sequences of tasks that could result or be tested: path A 422 which executes tasks 428, 430, 432; path B 424 which executes tasks 446, 448; and path C 426 which executes tasks 450, 452 and 454. Paths A and B are feasible paths where-in the assignment of resources 406 enables patient care. These paths are calculated as feasible a priori to the time they are actually executed. Path C is a path that, for example, a user provides specific direction for. An example of a cause for such an over-ride of the control system's assignments is an emergency medical condition that a doctor or staff in a centralized control center orders. The disclosed system enables an efficient recovery from such an intervention via the automatic re-optimization of resource assignments 406 and paths 420.

Returning to the example, the goals of the control system are to lower the average of, or reduce the measure of a metric such as the length of stay of patients over an interval of time or the wait time of patients for scheduled services over a time interval. These goals are realistically bound by constraints such as the number of resources made available for the execution of the tasks and multiple criteria for the performance of the healthcare delivery operations. The system and method disclosed herein takes as an input from the health system, what the resources are 406, their availability through time and the preferences of management with respect to the ratio of throughput and schedule risk criteria.

The time to complete a care plan, for example, between ending point 410 and starting point 407 is desired to be minimized so that the length of stay is reduced and average wait time for procedures is also reduced. These outcomes are achieved with efficient resource assignments and task sequencing of the activities related to a plurality of patients 402, 404 that share the resources 406 through time.

Figure 5:
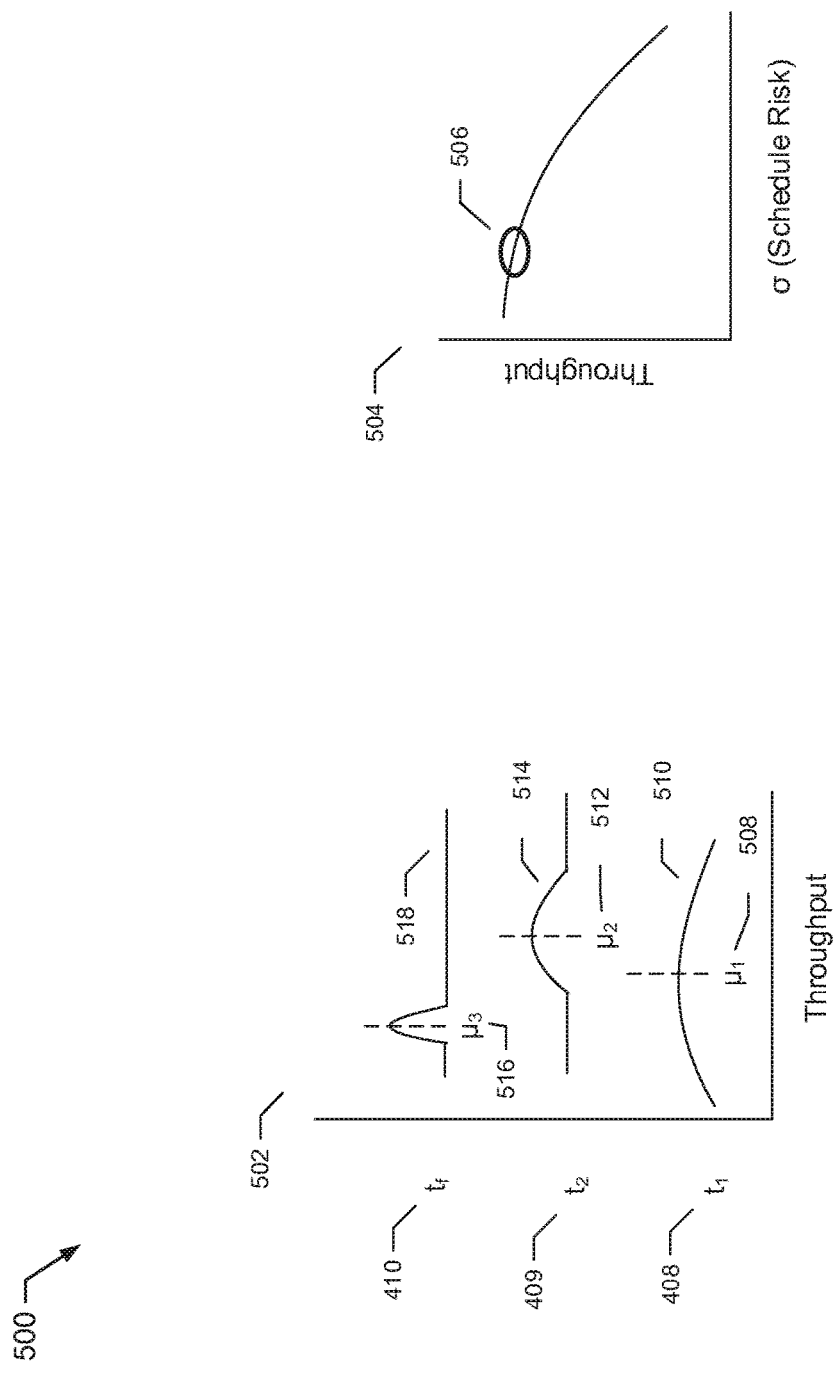
FIG. 5 shows examples of throughput and schedule risk in an example cross-system probabilistic alerting and activation system, according to the present disclosure.

Referring now to FIG. 5, the care tasks, such as an exemplary one at 502 have variation in their duration. This variation results from the skill of the care provider, the attributes of the patient, availability or performance of the resources needed for the protocol step, for example. Traditionally, these factors which cause duration estimation variance are accounted for by adding slack time into the schedule such that an average time duration is used in the scheduling of workflow or that there is an added increment of time in or between procedures to account for schedule risk. It is the summation of these slack times that accumulate and constrain highly interdependent schedules that have a high coupling to shared resources and whose activities have variation. This constraint and delay aspect of the physical system occurs because of the many critical paths that bind the release of shared resources. For example, an operating room can be used by only one patient and a set of surgeons, nurses and apparatus at a time. A second patient's operation cannot start until some or all the resources are made available. If a first operation runs late, a second operation cannot occur. If a first operation has variation, the second will likely not finish on time either. A third or fourth or more operations that rely on shared resources will also likely be delayed. These delays are targeted for reduction by managing the tasks and resources concurrently. The average duration for a type of task is desired to be reduced. The variation of time and thus schedule risk, σ, which is the deviation from a scheduled start or finish time, is desired to be reduced. Wait times are a byproduct of unscheduled variation. Throughput of patients is desired to increase. However, where the institution is comfortable balancing the relationship of throughput and schedule risk 504 as a preference, criteria or goal 506, the present control system seeks to achieve that ratio 504 through the automatic assignment of assets or targeted user intervention via a shared decision making capability, such as the Command Center. The shape of the relationship 504 may take many forms. Ideally the system control can achieve maximum throughput with minimal risk. If this attribute is possible with the health delivery system, then it would be highly desirable to control the system to this ideal state. Due to the attributes of the tasks, resources and variations, the relationship of throughput and variation may be such that there may not be an operating point where schedule risk and throughput are jointly optimal. For example there may be a zone of variation where throughput is highest, yet the highest throughput only occurs in a narrow window of risk. The health system management would set its preference for risk or throughput. The disclosed control system will cause the resource assignments to approach the selected preferences of the throughput mean, $\mu$, schedule risk, $\sigma$, throughput, and throughput/risk trade-off value 506.

The disclosed system beneficially updates the variation in task time 502 as the actual world unfolds from time before activities occur 407, through time at $t_1$ 408, $t_2$ 409 and $t_3$ 411. At $t_1$, the average duration forecast $\mu_1$ 508 and probability 510 is known with an estimate that may have significant variation, where-as after tasks 412 and 418 complete and their actual duration as oppose to their forecasted duration is realized at $t_2$ 409, the time forecast for the future task becomes comparatively more certain 514 with a revised average duration $\mu_2$ 512. The reason why this revised forecast comparatively improves, relates to the allocation of interdependent resources 406 in tasks prior to, being more fully realized. At $t_3$, after tasks 414, 416 even more tasks have realized and thus the variation of interdependencies which could delay activities at 502 are being reduced. The ending time $t_f$ 410 is thus dependent on paths 422, 424 and 426. The user intervention into the operations 426, is an exogenous factor that the disclosed system enables and to recover from, but does not explicitly forecast other than through the historical variation observations 450 used to establish the current task variation forecasts. Thus the forecast for completion at step 456 is a function of the duration estimations for path A 422 and B 424.

Figure 6:
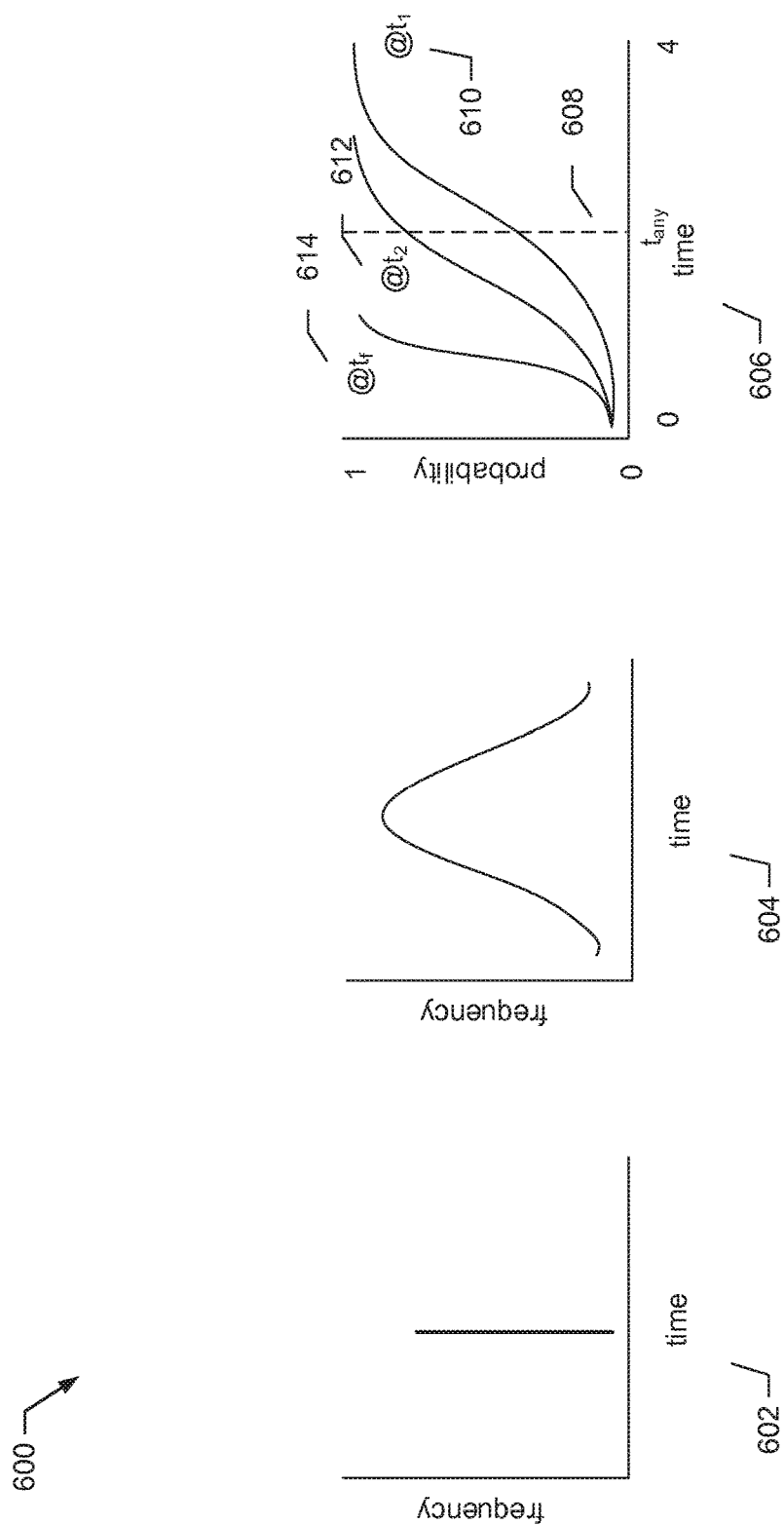
FIG. 6 shows examples of a delivery system with no variation, with variation and the probability density function in an example cross-system probabilistic alerting and activation system, according to the present disclosure.

Referring to FIG. 6, in an idealized delivery system with no variation, the system scheduling and actual realization occurs exactly the same 602. In the real world, tasks have variation and thus the finish 456 has a variation in finish time 410 as depicted in the histogram 604 of frequency and time. This histogram is converted into a probability density function and then integrated to achieve a cumulative probability function 606 which characterizes the relationship between completion probability and time. Time may be an absolute duration or the gap between a schedule and actual realized time or simulated time.

The task duration estimation is probabilistic 502 and is forecasted by one or any combination of four methods: actual sensed progression 724, historical duration 730 for the task that is repetitive, inference from like past observed durations 736 at a given institution or optionally from other relevant enterprises as directed by the system if insufficient native historical observations are lacking, user expertise 744 and simulation 740 such as a discrete event and agent-based methods that are virtually orchestrating some or all of the protocols and activities.

In the protocol is a conditional step 420 where in it is possible to direct the flow of tasks in a different order or call different tasks all together. The duration of those sequences is determined with the forecasts for tasks organized in a critical path. At the conditional step 420, a path is chosen 422, 424 as a function of the objectives of the health system management with respect to throughput and schedule risk, $\sigma$, as examples of objectives. $t_f$ 410 is thus characterized for each path 422, 424 and a most optimal path is implemented by the control system at 420 and therefore a comparatively more accurate forecast mean 512 and variation 514. With that added precision, all other managed tasks and resources for other patients are updated and their forecast errors are also lowered.

There can be any number of conditional routing points 420 and tasks. The resulting end point 456 completion with respect to time 410 will be forecasted through a full enumeration of the available paths and the path tasks. The probability 606 of time is calculated by forecasting each task duration using one or any combination of history, inference, process simulation and user judgment and then full enumeration through the conditional branches 420 and the constraints-based structure to derive the critical path duration. Replications are made of all tasks and forecasts with a Monte Carlo wrapper. The duration estimation 610 for all probabilities 606 at time $t_1$ 610, at time $t_2$ 612 and time $t_3$ 614. The span of duration for each of the three curves is duration and schedule risk. The point at which the throughput and schedule risk is acceptable 608 is selected so that the main outcomes desired, such as, for example average length of stay and wait time is achieved.

IV. Example Method

The above discloses the way to aggregate cross functional task, decision, and state information for the purposes of improving hospital operations management by better understanding which patient will consume what resources in specific tasks and by enhancing the accuracy of assumptions of the constraints-based scheduler/dynamic scheduler with simulation that is informed by cross departmental status information. Decision makers from one or more functional departments can thus benefit from a trusted, comprehensive set of facts that produce better assumptions for forecasting and optimizing control of activities in their departments. The decision makers can over-ride the automatic capacity and dynamic workflow control, for example, when non-computable information or judgment is provided to the one or more decision makers who thus have superior context from which to then make informed local and global operations decisions and also have input into clinical decision makers who, synthesizing this information may change clinical care paths to incorporate operations opportunity or constraints. Examples of having information that would provide a superior operations decision from a user judgment intervention would be event data such as a large accident or a dignitary visit or a localized breakdown in capacity that must be given time to recover operations.

While having global, local, and probabilistic information for past, current and forecasted future improves the decision making across functional bounds of a hospital's operations, it is can also be appreciated how optimally selected pathways of alternative sets of pathways would expedite the hospital operations decisions. In other words, by knowing the probabilistic outcome of making a decision BEFORE a decision is made, i.e., how it will effect both other patients, the current patient's outcome, and hospital operations and resources has a profound effect on the decision being made. This type of decision cannot be made by humans alone, but only with the tools presented in the current disclosure which are able to simulate thousands of dependencies over multiple time ranges, across the functional departments of a hospital, automatically search the candidate space and optimally find the best (lowest cost, lowest patient wait state time, highest hospital capacity and any number of one or multiple criteria, for example) and then automatically control the allocation of resources to achieve the optimization objective(s).

Figure 7:
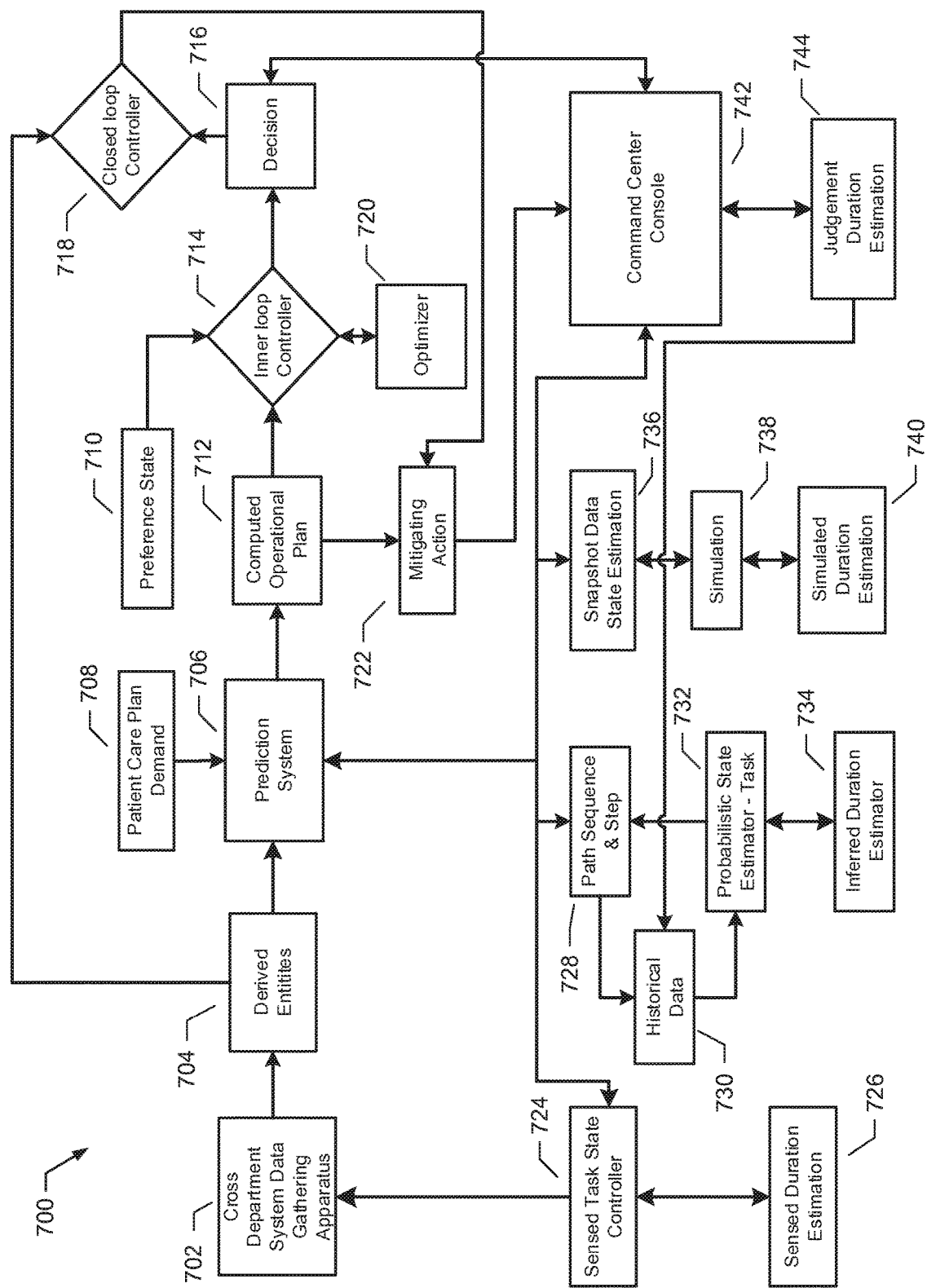
FIG. 7 shows examples of a method of creating predictive forecast assumptions used in the direction of people, assets and consumables in an example cross-system probabilistic alerting and activation system, according to the present disclosure.

FIG. 7 illustrates a flow diagram of probabilistic cross-system forecasting, alerting, control optimization and activation system 300 according to one aspect of the present disclosure. In healthcare operations, activities such as skilled care delivery, medical tests, medications delivery, and therapy, as well as other additional clinical procedures are orchestrated so as to heal the patient. Hospital operations seek to efficiently deliver this care at high standards, with pathways and protocols delivered in a timely manner. In certain aspects, there may be a generic structure to these clinical tasks and decision points as well as nested and conditional branches to handle unforeseen variations each circumstance presents.

The method 700 of creating predictive forecast assumptions used in the direction of people, assets and consumables by the disclosed hospital operations control systems and then monitoring the resultant specific actions those resources take through time with respect to their specific locations and duration direction in response to the initial control direction, and then dynamically corrected if the actual hospital operation deviates from the 'control signal' is discussed. In certain aspects, the probabilistic cross-system forecasting, alerting, optimization and activation system 300 uses two operational control and optimization loops to manage hospital activity— an inner loop allocates the resources of care such that the reference states and the state condition limits of those resources is met and not exceeded while an outer loop assures that the hospital operations are progressing through time as required to achieve delivery of the specified care in the allotted time duration within the variable cost constraints of the enterprise. System 700 provides predictions of the care delivery process and resource state information, automated control of resources and assets in the care delivery process as well as receiving the user in the loop inputs and manages health system assignment outputs in response to the automatic operations control or "what-if" scenario based decision support.

Cross department system data gathering apparatus 702 provides system-wide data which is collected and collated from the enterprise's specific departmental clinical applications, machines, and dedicated control sensors deemed to be relevant to hospital throughput and safety control. These data are made accessible to the staging and production environments. From these environments, derived entities 704 for use in computation of task, resource and location attributes of the care workflow are calculated. One consumer of this operational feedback data is prediction system 706 and another is closed loop controller 718 to assure the specified workflows, tasks, and actions are in fact, occurring in the temporal and spatial domains as anticipated by prediction system 706.

In certain aspects, prediction system 706 is comprised of four analytical sub-processes and is provided a patient care plan demand 708 to which the hospital operations controller will optimally and probabilistically solve for on a continuous basis in response to an ever-changing presenting number of scheduled patients, their required care and the changing states of care providers as assets. A preference state 710 of the hospital resources with respect to patient care delivery and safety are provided for by an inner loop controller 714 which in certain aspects, utilizes optimizer 720 to resolve a computed operational plan 712 against the desired preference state 710 of the resources used in care delivery such that locations, duty cycles and sequences of the enterprise's care delivery resources are met in a duration of time being controlled for, which may span a period of time from the instant to the next shift, to days ahead. The beneficial result is that patient throughput is optimized while resources such as persons, equipment, consumables and physical space do not exceed their safe operating points so that care delivery defects are avoided. The present control system can automatically lower the care demand of executing tasks by targeted healthcare providers or receive an over-ride by decision makers for the purposes of allowing care providers more time to execute the requisite clinical protocols in a manner that more completely enables the full protocol to be safety delivered. The care defect feedback loop is derived from sensing systems, such as optical based. When the defect rate is reduced, the workflow may then be controlled to a higher throughput or intensity and/or at fewer wait states.

Tasks, locations, and resources are controlled by the disclosed system in an automated manner yet the direct user decision is also implementable within the dynamic control in such a way as to enable the change of direction that either agrees with the automated control system or over-rides them and still protects the operational system outcomes. Automated and user decisions 716 with respect to tasks, locations, and time are made and automatically disseminated to the resources of care, such as via a computer they are interacting with or an on-body device such as a smart phone or other input/output device. While it is desired that the resources of care respond to their control directives, since hospital operations are a dynamic system with ever-changing states of health, resource availability and human capacity—the disclosed system beneficially anticipates that the actual processes as compared to the requested actions will vary. This feedback is reconciled in closed loop controller 718 with a comparison of desired location and task state with actual locations and state from the enterprises' cross department system data gathering apparatus 702 through derived entities 704. An alert 722 is provided when the current derived entities 704 and predicted computed operational plan 712 diverge in terms of actual differences or forecasted operational risk or when infeasible operations are detected in the instant and through the forecast interval.

In certain aspects, prediction system 706 integrates four prediction types. A first approach is direct sensing of controlled activities, resources, and assets via sensed state task state controller 724. Sensed state task controller 724 uses estimated sensed duration information 726 from RFID, optical based reasoning, Doppler radar based and other modalities such as pressure, temperature, embedded equipment sensing, mobile input from consumer electronic devices such as smart phones and computing devices, for example. The input data are provided to cross department system data gathering apparatus 702 for use by prediction system 706. Sensors such as optical and Doppler as well as edge computing devices such as smart phones have computing capabilities that are now and can be programmed to include a prediction of state over a forecast interval and provide that prediction to compute an operational plan 712 via prediction system 406.

A second approach is precedence and antecedent based task and resource probabilistic constraints-based method whose tasks are temporally ordered and whose fulfillment is conditioned upon resource availability. A simple example of such method is a Gantt analysis, however the deterministic limitations of that method are overcome with the present system which uses probabilistic durations for tasks and thus solves for probability of completions and schedule risk. For each path sequence and step 728, historical data 730, for example, task duration, is characterized and fit into a probability distribution for likely duration of that task. A correction is made to narrow the duration estimation variance based upon the elimination of sample points related to task patterns such as workflows, whose paths are unlike the current plan of task sequencing, time, resources, and entities being processed in probabilistic state estimator 732. Inferred duration estimator 734 then estimates the duration for a sequence of tasks which is then provided as a prediction to the computed operational plan 712. An inference may be made when there are not historical exact conditions to the current. The root data for such inferences may be recalled from the present health system or another like system as selected by the system's logic or an analyst.

A third approach is a simulation method 738 whose assumptions and state information 736 is updated from the enterprise's cross department system data gathering apparatus 702 and derived entities 704. Simulation method 738 is discrete event or agent based or a hybrid combination of agent and continuous simulation methods. Updated derived entities 704 are provided to prediction system 706 which, in turn, provides an update of the current state of the hospital resources being controlled and receives a patient care plan demand forecast 708 to which the balance of the disclosed health discovery system control automatically satisfies, given the state constraints and objectives of preference state 710. Simulation method 738 predicts the resource location and task duration performance over the forecast interval and provides the simulated duration estimation 740 to computed operational plan 712.

A forth approach is the expert opinion of one or more persons connected to and communicating with command center console 742 whose configurable interfaces enable the output of the disclosed decision support, the input from the expert(s) individually or reconciled together amongst stakeholders, for duration estimation 744 and/or confirmation of the automated process control commands which are then promulgated across departments.

Each prediction of resource, patient, and physical space's use or task duration through the specified forecast interval, may be taken individually or fused with statistically averaged or majority win or weighted composite or probabilistically aggregated through a closed form or Monte-Carlo means in order to derive a duration forecast value range estimation as an input into computed operational plan 712. Comparison of the demand from a patient care plan 708 to the computed operational plan 712 is conducted by prediction system 706 which resolves the forecast from which the resources are controlled in inner loop controller 714, and subject to preference state 710 and decision 716 which can either be an automated system decision or based on user intervention from the command center console 742, for example.

The disclosed cross departmental system provides situational awareness of the enterprise activity status, for example, the tasks and locations of care delivery and resource state information such as availability, location, cumulative wear or damage with respect to its maintenance plan; physical space via physical command center console 742 which contain reconciled and integrated displays. The data and analytical sequences in the disclosed control system may be configured as a series of web services to make the Command center console 742 accessible on computer networks either wired or wireless, using a computer or mobile devices, to view and/or provide input to drive the direction of people, assets and consumables in hospital operations.

For example, a plurality of patients 804 present at a care delivery institution, some of whom are scheduled while others arrive due to unplanned medical circumstances. A number of patients out of the population of presenting patients 804 may have a similar care pathway specified upon their initial evaluation result. There may be any number of patients 804 who could present with a known diagnosis but whose admittance is "gated" so as not to overwhelm the hospital's capacity. Having a similar diagnosis a sequence of patents 804 engage the care process beginning with a first task 806, transferring to a second task 808, next proceeding to a third task 810 before a clinical decision 814 is made.

A decision may result in one or more resultant next sequence of tasks 814. In certain aspects, the decision D2 (812) of sequence of tasks 814 involves task T6 (816) whose successor decision D4 (818) resulted in a referral R1 (820) to another clinician for decision D1 (822) with a likelihood to progress to either task T2 (808) or T3 (810) at a priori probabilities P1 (824) and P2 (826) respectively. For the locations, staff, and specialized assets used in T2 (808) and T3 (810) it is advantageous to know when, for example, patent 801 would conditionally use those clinical services given that other patients such as patient 802, are also processing through care delivery process 800.

The probability of patient 801 proceeding on path 820 towards D1 (822) is estimable at the conclusion of task T3 (810) before D2 at one level and significantly improves after D4 (818) and further improves to near certainty after D1 (822). System 800 tracks the change in path probabilities such as P1 (824) and P2 (826) through time. Forecasted probabilities are derived from historical patterns and inferred with statistical confidence intervals or made explicit should a clinical decision/assessment be made. The specific and aggregate clinical pathways are thus dynamically assessed and tracked in order to improve the demand estimation in terms of quantity and time for the various operations in the hospital.

In certain aspects, there are a multitude of operations, such as transports, tests, medications, therapies Tn (828) that are tracked, executed, and computed over time, place, asset, people, as "tasks". A task is an activity that consumes time, location, people, consumables, and/or assets for a duration. The duration has a desired start and forecasted end time.

Figure 9:
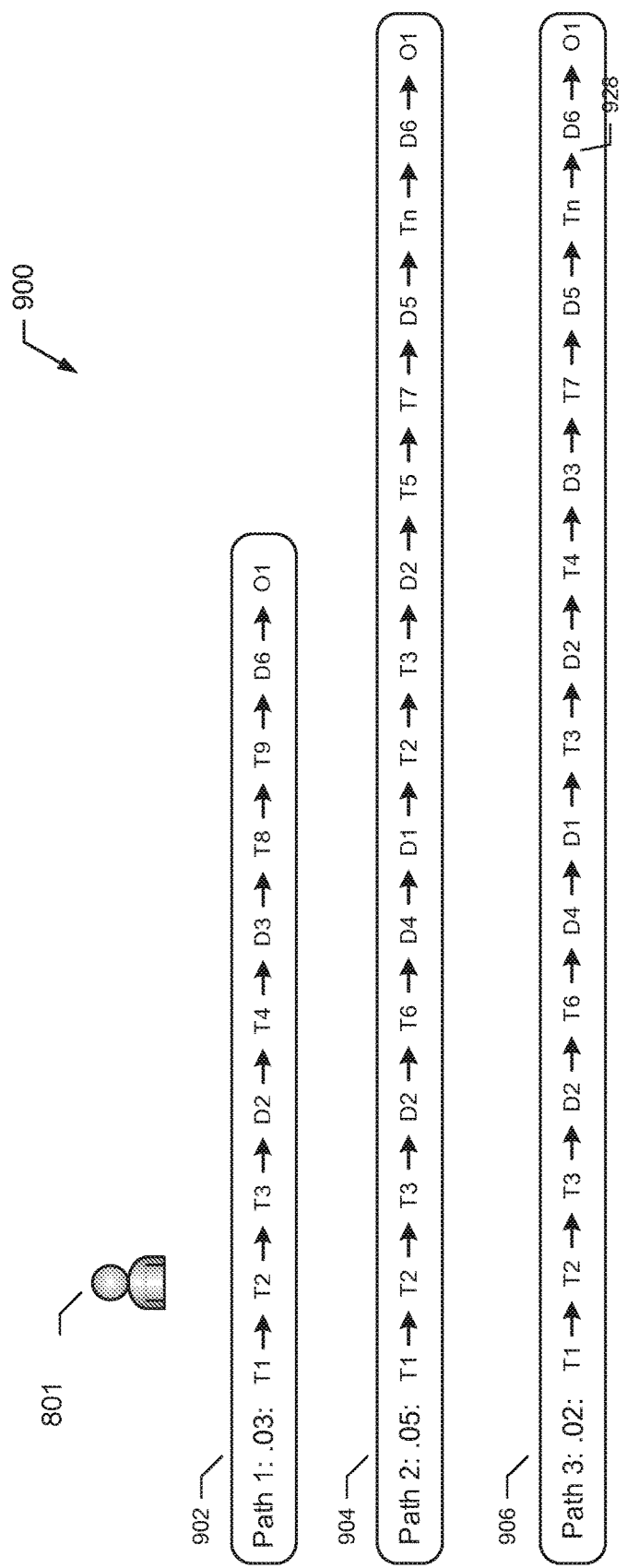
FIG. 9 show an example path enumeration and probability estimation method.
Figure 10:
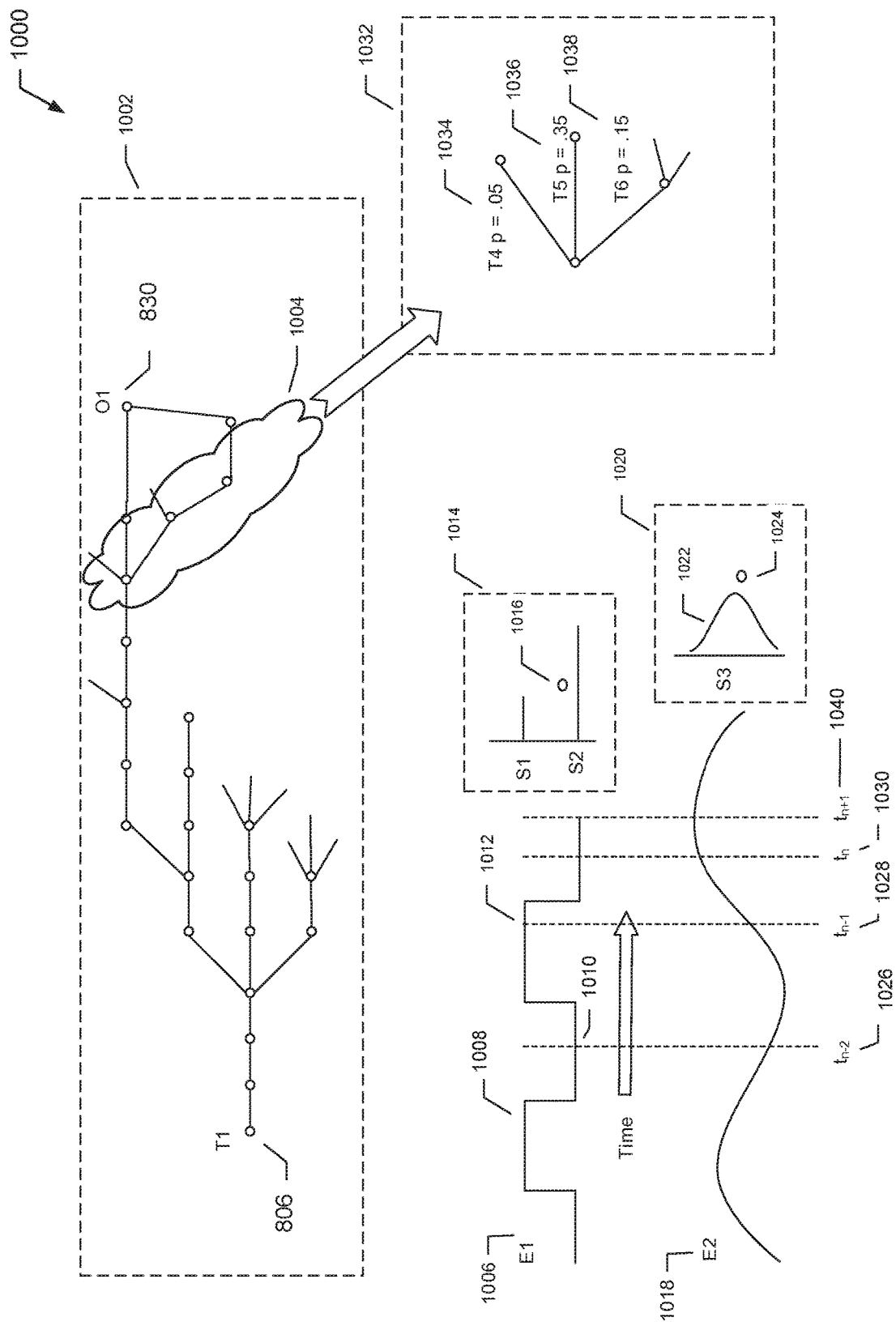
FIG. 10 shows an example network diagram for feasible paths of an example system.

Referring to FIG. 9, the path enumeration and probability estimation method 900 is disclosed. The clinical pathway that patients realize may be many. Each path has a different consumption of resources and is a function of its sequence. The sequence results from a plan and changes to a new plan as a result of a change in a patient's health state or the effects of a factor on the availability of resources to achieve a path or the conditional use of a path by other patients as necessitated by their comparative health state. Updating where a patient is on a clinical path enables more precise allocation of resources.

Patients 804 present to the health system care providers and a resulting set of diagnosis results, from which a care plan for each patient's condition is established. The plan may evolve at any time. The probability that the exact pathway trough the hospital for the duration of the treatment will be precisely known at admission is low and thus reconciling future conflicts for the use of a certain asset or resource has a high variability of certainty at an initial time. This imprecision prevents a firm resource allocation and in the prior art is compensated for by building in the wait times and buffers in schedules. Typically these buffers are scheduled as slack time. It is the accumulated effects of this slack time that the present invention targets to reduce so as to increase throughput and lower the incidence of waiting. To achieve this aim, a schedule is made to be dynamic, conditional and probabilistic versus a schedule set at admission. Hospital activities are thus actively controlled to advance the totality of protocols in the enterprise not based upon set schedules but to progress as the resources and patient states are able to. The probabilities for durations and responses are required to reduce errant assignments and thus the most accurate and current probabilities are derived on a continuous basis so as to reduce control error.

In FIG. 9 an example of a single patient presenting with a diagnosis is used to illustrate a number of sequences of a pathway, each with a probability and whose sum is 1. There is a determination that for similarly attributed patients and similarly available resources the patient 801 will traverse a first pathway 902 at probability 0.03; a second pathway 904 at p=0.05; a third pathway 906 at p=0.02, and a forth pathway 908 at p=0.9. The forth pathway 908 is known with high confidence through the first three tasks T1, T2, and T3, up to decision point D2, then depending upon the clinical or operational decision at D2 (814), the patient 801 may then proceed to thousands of other paths at 0.9 probability. The remaining 0.1 probability results from the sum of the three fully enumerated paths 902, 904, & 906 whose probabilities of realization sum to 0.1

Typically patients will traverse the institution to receive care 806 and then discharge 830—thus the probability of proceeding through all feasible care paths is 1. The network diagram 1002 for feasible paths is extensive. As an example, a single decision point 1004 to disclose the mechanism of dynamically updating the probability of a patient being on a given path is shown.

Paths change by design in response to the patient's clinical response to care and because of the resource availability used to deliver tasks and decisions in care plans. For example, a factor E1 1006, whose pattern overtime is characterized by 1008, 1010, and 1012. The factor may be any one of hundreds, but for illustrative purposes, it may represent the availability of a particular resource that would enable tasks at 1008 and 1012. if a controlled resource is not available, those associated tasks cannot be performed. A different clinical or operational decision would thus likely be made and the patient would experience a different clinical pathway.

In certain aspects, there are two states, S1 and S2 for exogenous factor E1 1006: available (S1) or not available (S2). When a histogram is constructed of that state space 1014, there is a significantly greater portion of time in S2 than S1. When integrated to derive probability, the probability of being in S1 versus S2 is low. On average, E1 is available 1016.

Aspects disclosed and described herein provide the ability to attain cross departmental information to directly eliminate the forecast error difference between E1 being available on average 1016 versus being actually available at 1008 and 1012 which are explicit states and times so that a future path is determinable, actionable, and schedulable as a function and specificity commensurate with the confidence interval, which at all times is higher than the present art which uses deterministic durations and not continuously updated as the actual time unfolds nor through discrete or agent based simulation—whose assumptions and states are updated dynamically so that simulation based forecasts are also more accurate.

In another example, a different factor E2 1018 may be a patient's health state with respect to one or more clinical metrics or measures. As is the case with E1 1006, as time proceeds, so does the value of E2. The state S3 1020 of E2 when converted into a histogram then integrates into a probability density function 1022 and has a statistical mean value 1024. There is a forecast error between this average state variable S3 1024 and the probability that S3 may be anywhere in the state space defined by its probability density function 1022.

For a patient 801 at time zero, looking forward into a network of likely paths the probability of being realized through a specific path is characterized by 902, 904, 906, and 908. As an example, as clinical activity progresses, finishing task 3 at time $t_{n-2}$ 1026 with E1 1006 not available and E2 at an actual clinical metric level indication, the probability that any of the available clinical path enumerations is more determinable than at the start of T1 806. At a next time interval $t_{n-1}$ 1028, which for illustrative purposes is driving decision point D2 812, the probability of knowing which next step T4, T5, T6 improves in specificity.

At a time, for example "now" 1030, where decision point D2 is now known 1032 and the probabilities for which future path will realize change again. At $t_n$ 1030, it is 100% certain that a specific care path 1032 has been reached and an explicit path to the current location and care path is known. From past like-attribute patients it is 50% likely a care path through T4 and its successors 1034; 35% likely through T5 and its successors 1036; and 15% likely through T6 and its successors 1038. At the next time increment $t_{n+1}$ 1040, decision D2 and the next task are known, therefore the probabilities change again for the sequences of future tasks. This dynamic and ongoing aggregation of updates from across departments coupled with parsed down conditional or potential pathways as time is realized benefits the forecast accuracy with respect to hospital operations activity, staffing, and usage forecasting.

With the state of care pathways made explicit and the likelihood of future paths better appreciated across the various functions in the hospital, the demand estimates on future tasks, providers, assets is globally understandable and actionable by either the control system's automatic assignments or by user direction via the command center interface. Correct scheduling changes, putting the current patient on the optimal care path can thus be made with minimal or no disruption of the rest of the enterprise-wide system.

Thus, the disclosed cross departmental system provides an aggregate cross-functional task, decision, and state information for the purposes of improving hospital operations management by better understanding which patients will consume specific resources during each specific task. Human decision makers from one or several functional departments can thus use a trusted set of facts and better understand demand forecasts for the activities throughout their departments in the instances that the system's automated assignment control is intervened on. These decision makers can then make informed local and global operations decisions and also have input into clinical decision makers who, synthesizing the information may change clinical care plans to incorporate operations opportunities or constraints.

While having global, local, and probabilistic information improves the automated control of resources or the act of user decision making across functional bounds of a hospital's operations, it also demonstrates how optimally selected pathways or alternative sets of pathways would impact and expedite the hospital operations decisions.

Figure 11:
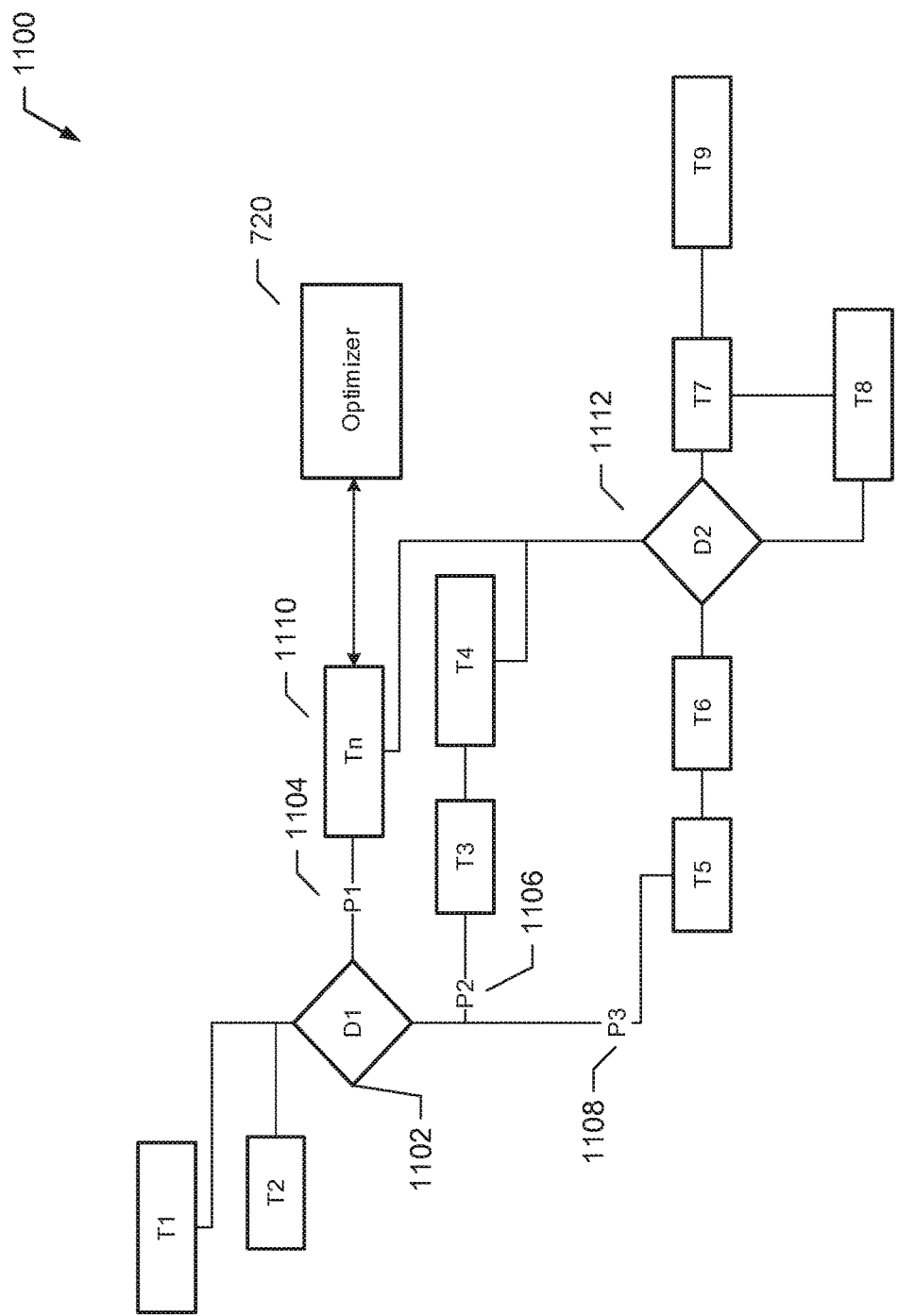
FIG. 11 show temporal and logical relationships incorporating the methods described herein across departments and time, thereby illustrating how the benefits of manual and automatic resource leveling and dynamic workflow and scheduling is benefited.

Referring now to FIG. 11, a set of decisions and tasks is arranged in sequence and time with antecedents and predicate relationships. The 'critical path' is desired to be known so that for operations purposes, workflows and schedules can be directed to achieve a task of decision point to occur at a beneficial point in time, thus managing the operational activities so as to achieve hospital throughput, minimize delays, improve resource utilization, lower costs and improve the patient's experience by proper expectation setting and communication of status.

Temporal and logical relationships are drawn 1100 incorporating the methods described above across departments and time, thereby illustrating how the benefits of manual and automatic resource leveling and dynamic workflow and scheduling is benefited.

Before decision point D1 1102, there are probabilities of three paths of tasks occurring before a second decision point is reached. Probability of a first path P1 1104, a second path P2 1106 and a third path P3 1108 may be known and an expected value for a cross function of those probabilities and the probabilistic sums of the tasks $T_n$ 1110 in each path to derive an expected duration.

Certain aspects of the present disclosure enable improving hospital operations by calculating the path dependent duration probability across departments. For example, a path P1 1104 is deemed to be viable and desirable for a given patient's care plan next steps. On path P1 is task $T_n$ 1110 whose parameters in terms of resource consumption and probabilistic duration are known. The use of task $T_n$ 1110 is checked for more optimal placement or resource scheduling by invoking an operations optimization engine 720. Task $T_n$ 1110 parameters are sent from the current hospital operations system to the optimization engine 720.

The current hospital operations system is comprised of cross departmental data 702 fed via messaging system such as one capable of interpreting HL7 messages for example, into a computer or server or cloud-based computing system and interfaced with one or more user interfaces 742.

Resource constraints, re-optimized workflow scenarios and schedule alternatives generated with the operations optimization engine 720 are made available via Command Center 742 or via computers and/or mobile devices for consideration by automated assignments or one or more decision makers or a hybrid of automation and user interactions—each method impacting one or more departments and the institution's capacity and/or safety at large. Decision D1 1102 and D2 1112 benefit from understanding how a decision made ahead of activity impacts the broader context and may choose one path over the other in response to stabilize operations or improve a patient's experience.

In reality, hospital operations decision makers are overwhelmed with the possible combinations of hundreds of patients and potential pathways, each with conditions and interdependencies. For example, in a hospital environment it can be conservatively estimated that it would take person years to compute and rank the possible combinations to choose the correct combination before the process of reconciling other person's opinions would begin. The present system calculates the comparative impact of one or more departmental delays or early finishes across the hospital's departments in approximately 22 seconds, solving with the objectives and constraints from more than one department or decision maker.

Figure 12:
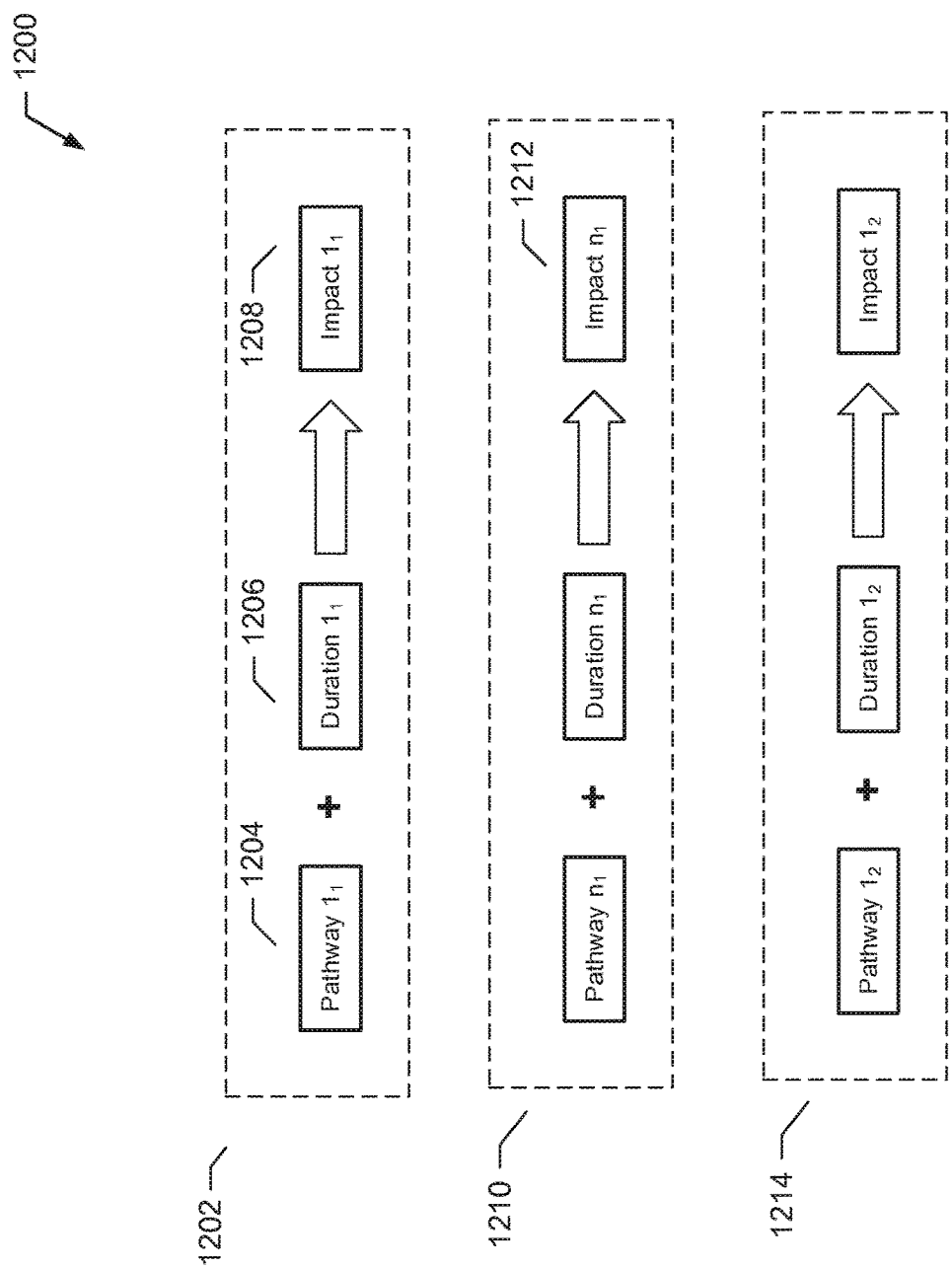
FIG. 12 shows a course ranking method for a dynamic environment spanning a plurality of time periods using an example impact metric related to time duration for services delivery which is typically a key hospital operations process indicator.

Referring to FIG. 12, a course ranking method 1200 is presented for a dynamic environment spanning a plurality of time periods using an example impact metric related to time duration for services delivery which is typically a key hospital operations process indicator.

At a first time, t, pathways 1202, 1210, of sequences of tasks and decision which can be taken for one or more patients are possible. A first pathway 1204 of tasks and decisions has a duration 1206 that consumes time and resources which impacts 1208 hospital operations. An alternate path 1210 results in achieving a clinical goal and consumes less time 1212 with equal clinical impact. The second path 1210 is sent to the operations optimization engine 720 for feasibility. In another example, a first 1202 and second 1210 path appear to be roughly equivalent clinically and it is desired to know which path is operationally superior. Both scenarios are passed to the operations optimization engine 720 for an assessment of schedule risk, cost or other operational criteria.

In the next instant of time 1214 the state of the hospital's care delivery flow changes and the evaluation process begins again; first with a rough estimate and then a precise evaluation of a subset of scenarios to calculate schedules, resource loading, and throughput, for example.

Departmental management typically ensures that service levels are met for clinical tasks conducted in those functional areas. The actions of one or more departments have an effect on other departments and thereby the overall hospital operations performance may degrade because the interaction effects were not used as a criteria in a department. Certain aspects of the present disclosure overcome these instances where 'locally' optimal or 'local' delays impact the broader institution since more informed clinical pathways, workflows, and schedules are enabled that more precisely place patients, providers, and assets for more coordinated operations.

Typical operations management systems monitor 'what is' such as bed occupancy and in some instances, infer the future state by using average durations for activities. Missing are considerations that multiple paths for clinical activity are included in those averages as well as task durations taken as average. The present system improves operations by considering paths, resource constraints and updates the forecast based upon cross-departmental status updates.

Flowcharts representative of example machine readable instructions for implementing the example system 300 of FIG. 3 are shown in FIG. 7. In these examples, the machine readable instructions comprise a program for execution by a processor such as processor 1312 shown in the example processor platform 1300 discussed below in connection with FIG. 13. The program can be embodied in software stored on a tangible computer readable storage medium such as a CD-ROM, a floppy disk, a hard drive, a digital versatile disk (DVD), a BLU-RAY™ disk, or a memory associated with processor 1312, but the entire program and/or parts thereof could alternatively be executed by a device other than processor 1312 and/or embodied in firmware or dedicated hardware. Further, although the example program is described with reference to the flowchart illustrated in FIG. 7, many other methods of implementing the example system-wide probabilistic alerting and activation can alternatively be used. For example, the order of execution of the blocks can be changed, and/or some of the blocks described can be changed, eliminated, or combined.

Figure 8:
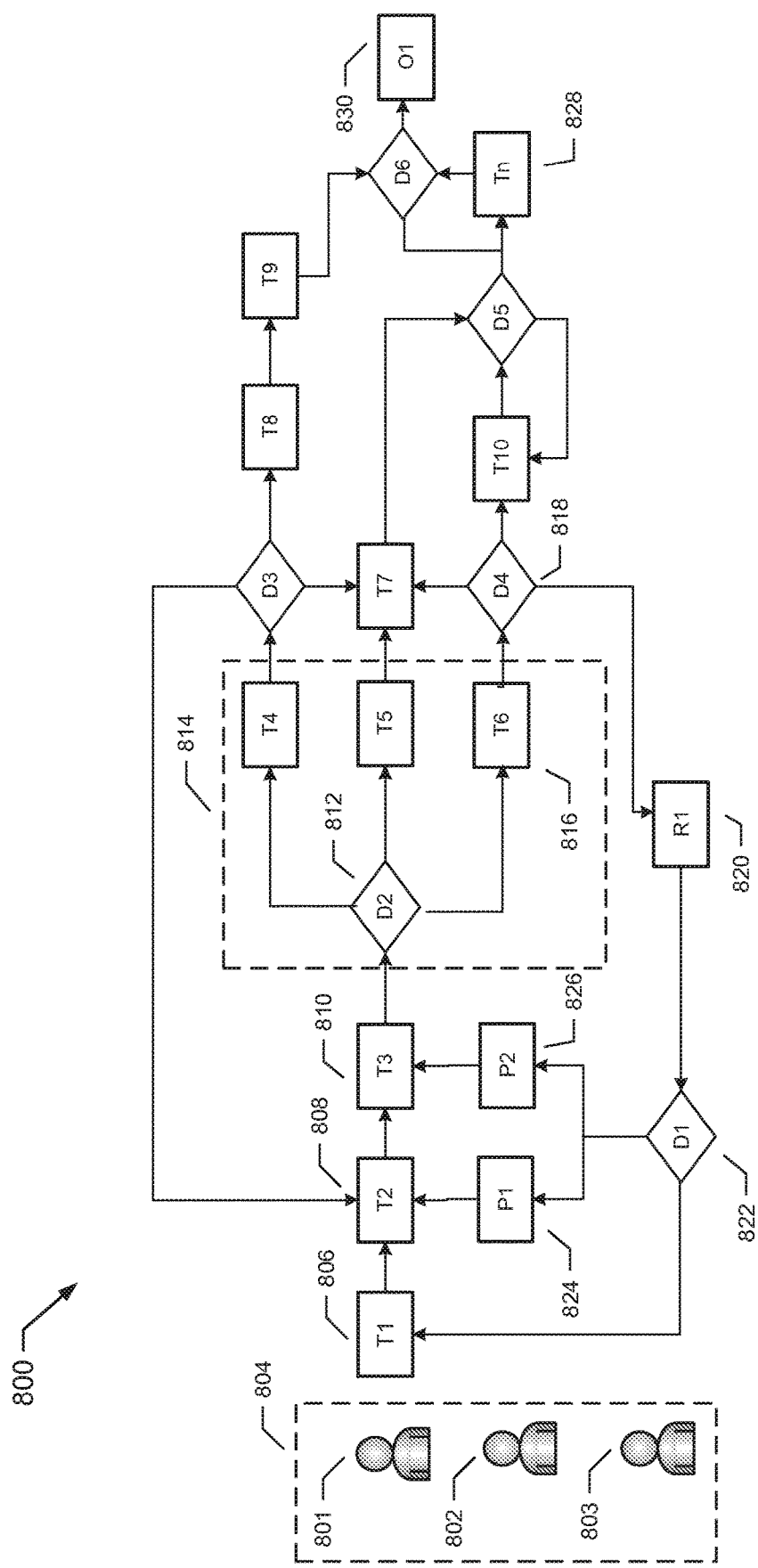
FIG. 8 shows an analytical flow diagram of the hospital control system in an example cross-system probabilistic alerting and activation system, according to the present disclosure.

As mentioned above, the example processes of FIG. 8 can be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example processes of FIG. 7 can be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used. herein, when the phrase "at least" is used as the transition term in a preamble of a claim, it is open-ended in the same manner as the term "comprising" is open ended.

V. Computing Device

The subject matter of this description may be implemented as stand-alone system or for execution as an application capable of execution by one or more computing devices. The application (e.g., webpage, downloadable applet or other mobile executable) can generate the various displays or graphic/visual representations described herein as graphic user interfaces (GUIs) or other visual illustrations, which may be generated as webpages or the like, in a manner to facilitate interfacing (receiving input/instructions, generating graphic illustrations) with users via the computing device(s).

Memory and processor as referred to herein can be stand-alone or integrally constructed as part of various programmable devices, including for example a desktop computer or laptop computer hard-drive, field-programmable gate arrays (FPGAs), application-specific integrated circuits (ASICs), application-specific standard products (ASSPs), system-on-a-chip systems (SOCs), programmable logic devices (PLDs), etc. or the like or as part of a Computing Device, and any combination thereof operable to execute the instructions associated with implementing the method of the subject matter described herein.

Computing device as referenced herein may include: a mobile telephone; a computer such as a desktop or laptop type; a Personal Digital Assistant (PDA) or mobile phone; a notebook, tablet or other mobile computing device; or the like and any combination thereof.

Computer readable storage medium or computer program product as referenced herein is tangible (and alternatively as non-transitory, defined above) and may include volatile and non-volatile, removable and non-removable media for storage of electronic-formatted information such as computer readable program instructions or modules of instructions, data, etc. that may be stand-alone or as part of a computing device. Examples of computer readable storage medium or computer program products may include, but are not limited to, RAM, ROM, EEPROM, Flash memory, CD-ROM, DVD-ROM or other optical storage, magnetic cassettes, magnetic tape, magnetic disk storage or other magnetic storage devices, or any other medium which can be used to store the desired electronic format of information and which can be accessed by the processor or at least a portion of the computing device.

The terms module and component as referenced herein generally represent program code or instructions that causes specified tasks when executed on a processor. The program code can be stored in one or more computer readable mediums.

Network as referenced herein may include, but is not limited to, a wide area network (WAN); a local area network (LAN); the Internet; wired or wireless (e.g., optical, Bluetooth, radio frequency (RF)) network; a cloud-based computing infrastructure of computers, routers, servers, gateways, etc.; or any combination thereof associated therewith that allows the system or portion thereof to communicate with one or more computing devices.

The term user and/or the plural form of this term is used to generally refer to those persons capable of accessing, using, or benefiting from the present disclosure.

Figure 13:
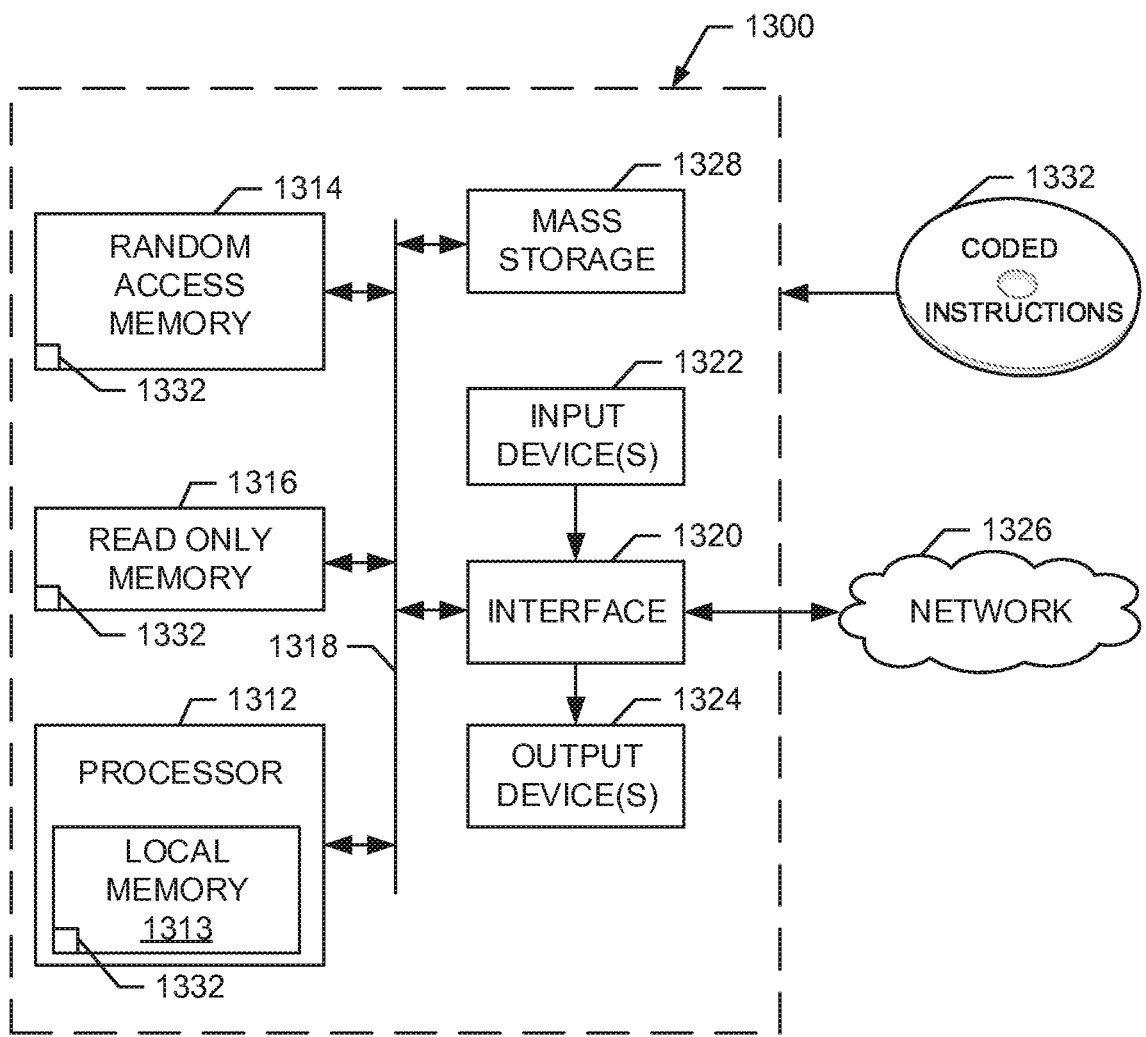
FIG. 13 shows a block diagram of an example processor system that can be used to implement systems and methods described herein.

FIG. 13 is a example block diagram of an example processor platform 1300 capable of executing the instructions of FIG. 7 to implement the example of FIG. 3. The processor platform 1300 can be, for example, a server, a personal computer, a mobile device (e.g., a cell phone, a smart phone, a tablet such as an IPAD™), a personal digital assistant (PDA), an Internet appliance, or any other type of computing device.

The processor platform 1300 of the illustrated example includes a processor 1312. Processor 1312 of the illustrated example is hardware. For example, processor 1312 can be implemented by one or more integrated circuits, logic circuits, microprocessors or controllers from any desired family or manufacturer.

Processor 1312 of the illustrated example includes a local memory 1313 (e.g., a cache). Processor 1312 of the illustrated example is in communication with a main memory including a volatile memory 1314 and a non-volatile memory 1316 via a bus 1318. Volatile memory 1314 can be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1316 can be implemented by flash memory and/or any other desired type of memory device. Access to main memory 1314, 1316 is controlled by a memory controller.

Processor platform 1300 of the illustrated example also includes an interface circuit 1320. Interface circuit 1320 can be implemented by any type of interface standard, such as an Ethernet interface, a universal serial bus (USB), and/or a PCI express interface.

In the illustrated example, one or more input devices 1322 are connected to the interface circuit 1320, Input device(s) 1322 permit(s) a user to enter data and commands into processor 1312. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 1324 are also connected to interface circuit 1320 of the illustrated example. Output devices 1324 can be implemented, for example, by display devices (e.g., a light emitting diode (LED), an organic light emitting diode (OLED), a liquid crystal display, a cathode ray tube display (CRT), a touchscreen, a tactile output device, a light emitting diode (LED), a printer and/or speakers). Interface circuit 1320 of the illustrated example, thus, typically includes a graphics driver card, a graphics driver chip or a graphics driver processor.

Interface circuit 1320 of the illustrated example also includes a communication device such as a transmitter, a receiver, a transceiver, a modem and/or network interface card to facilitate exchange of data with external machines (e.g., computing devices of any kind) via a network 1326 (e.g., an Ethernet connection, a digital subscriber line (DSL), a telephone line, coaxial cable, a cellular telephone system, etc.).

Processor platform 1300 of the illustrated example also includes one or more mass storage devices 1328 for storing software and/or data. Examples of such mass storage devices 1328 include floppy disk drives, hard drive disks, compact disk drives, Blu-ray disk drives, RAID systems, and digital versatile disk (DVD) drives.

Coded instructions 1332 of FIG. 5 can be stored in mass storage device 1328, in volatile memory 1314, in the non-volatile memory 1316, and/or on a removable tangible computer readable storage medium such as a CD or DVD.

VI. Conclusion

Thus, certain examples provide a clinical knowledge and control system that enables healthcare institutions to improve performance, reduce cost, touch more people, and deliver a higher quality of care because more aspects of the protocols are executed, across the departments of the enterprise. In certain examples, the clinical knowledge and control system enables healthcare delivery organizations to improve performance against their quality targets, resulting in better patient care at a low, appropriate cost.

Certain examples facilitate improved control over process. For example, a healthcare operations control system including a prediction engine integrating data from one or more departments and healthcare systems in a healthcare environment is enabled for the control of operational throughput, wait-times, and schedule risk. The example control system also includes identifying controllable and non-controllable resources and a plurality of conditional and non-conditional clinical protocol tasks which are subsequently directed. The example control system also includes receiving one or more operating objectives related to one or more of operational throughput, wait-times, and schedule risk and monitoring the execution, with respect to the objectives, of the plurality of clinical protocol tasks in a clinical environment by the care delivery resources including people and physical assets. The example control system further includes predicting a) activity of the one or more care delivery resources and patients in the plurality of clinical protocol tasks for one or more time periods and b) a change of activity of patients and care delivery resources with respect to the clinical protocol tasks over a selectable interval of time. The example control system also includes automatically optimizing present and future actions of the controllable care delivery resources to mitigate the predicted non-value-added idle time, throughput constraint and workload of care providers to control a flow of patients through clinical protocols and a risk of achieving specified resource efficiency across the plurality of clinical protocols. The example control system additionally includes triggering the one or more mitigating actions with the respect to the plurality of clinical protocols; and monitoring effects of the mitigating actions and adjust resource assignments based on the effects of the mitigating actions.

Certain examples leverage information technology infrastructure to standardize and centralize data across an organization. In certain examples, this allows for cross-system probabilistic alerting and activation that automatically controls the resources and conditionally allocates capacity across departments to achieve a minimal wait state through an interval of time.

Technical effects of the subject matter described above may include, but is not limited to, providing system 300 and method 700 which allow for cross-system probabilistic alerting and activation that automatically controls the resources and conditionally allocates capacity across departments to achieve a minimal wait state through an interval of time.

Moreover, the system and method of this subject matter described herein can be configured to provide an ability to better understand large volumes of data generated by devices across diverse locations, in a manner that allows such data to be more easily exchanged, sorted, analyzed, acted upon, and learned from to achieve more strategic decision-making, more value from technology spend, improved quality and compliance in delivery of services, better customer or business outcomes, and optimization of operational efficiencies in productivity, maintenance and management of assets (e.g., devices and personnel) within complex workflow environments that may involve resource constraints across diverse locations.

This written description uses examples to disclose the subject matter, and to enable one skilled in the art to make and use the invention. The patentable scope of the subject matter is defined by the following claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A computerized healthcare operations control system comprising:
   at least one processor to implement at least:
   a plurality of first controllers to allocate a plurality of resources in locations of a healthcare facility to execute a process according to reference states associated with the resources and condition limits bounding the reference states for the respective resource, the plurality of first controllers to manage the allocation of the plurality of resources to maintain the condition limits bounding the reference states for the respective resources so that the respective reference state does not exceed the corresponding condition limit for the respective resource;
   a second controller to monitor the resources allocated by the plurality of first controllers with respect to completion of a process, the second controller to predict a time of completion of the process by the resources and to provide feedback to one or more of the plurality of first controllers when the predicted of time of completion exceeds an allotted time duration for the process, the respective one or more of the plurality of first controllers to adjust a configuration of at least one of the plurality of resources based on the feedback from the second controller.

2. The system of claim 1, wherein the feedback from the second controller to one or more of the plurality of first controllers is to adjust the allocation of resources from a first resource lacking capacity to a second resource with available capacity.

3. The system of claim 1, wherein the condition limits bounding the reference states for the resources include a capacity limit and a wait time threshold.

4. The system of claim 3, wherein the condition limits trigger one or more of the plurality of first controllers to allocate resources to achieve a minimum wait state through an interval of time based on the feedback from the second controller.

5. The system of claim 4, wherein the allocated resources are located in a plurality of departments of the healthcare facility.

6. The system of claim 1, wherein the process includes a plurality of clinical protocol tasks to be executed by the resources, and wherein the second controller is to predict a) activity of the resources in the plurality of clinical protocol tasks for one or more time periods and b) a change of activity of the resources with respect to the plurality of clinical protocol tasks over a selectable interval of time.

7. The system of claim 1, wherein the plurality of first controllers is to resolve a computed operational plan defining the process against the reference states of the resources allocated to execute the process so that locations, duty cycles, and sequences of the resources are met within the condition limits and the allotted time duration for the process.

8. A computer-implemented method for controlling healthcare operations via a configured processor, the method comprising:
    allocating, by a plurality of first controllers, a plurality of resources in locations of a healthcare facility to execute a process according to reference states associated with the resources and condition limits bounding the reference states for the respective resource;
    managing, by the plurality of first controllers, the allocation of the plurality of resources to maintain the condition limits bounding the reference states for the respective resources so that the respective reference state does not exceed the corresponding condition limit for the respective resource;
    monitoring, by a second controller, the resources allocated by the plurality of first controllers with respect to completion of a process;
    predicting, by the second controller, a time of completion of the process by the resources; and
    providing, by the second controller, feedback to one or more of the plurality of first controllers when the predicted of time of completion exceeds an allotted time duration for the process, the respective one or more of the plurality of first controllers to adjust a configuration of at least one of the plurality of resources based on the feedback from the second controller.

9. The method of claim 8, further including adjusting, based on the feedback, the allocation of resources from a first resource lacking capacity to a second resource with available capacity.

10. The method of claim 8, wherein the condition limits bounding the reference states for the resources include a capacity limit and a wait time threshold.

11. The method of claim 10, wherein the condition limits trigger one or more of the plurality of first controllers to allocate resources to achieve a minimum wait state through an interval of time based on the feedback from the second controller.

12. The method of claim 11, wherein the allocated resources are located in a plurality of departments of the healthcare facility.

13. The method of claim 8, wherein the process includes a plurality of clinical protocol tasks to be executed by the resources, and wherein the second controller is to predict a) activity of the resources in the plurality of clinical protocol tasks for one or more time periods and b) a change of activity of the resources with respect to the plurality of clinical protocol tasks over a selectable interval of time.

14. The method of claim 8, wherein one or more of the plurality of first controllers is to resolve a computed operational plan defining the process against the reference states of the resources allocated to execute the process so that locations, duty cycles, and sequences of the resources are met within the condition limits and the allotted time duration for the process.

15. A non-transitory computer-readable storage device having a set of instructions for execution on a computer, the set of instructions, when executed, causing and configuring the computer to implement a method, the method comprising:
    allocating, by a plurality of first controllers, a plurality of resources in locations of a healthcare facility to execute a process according to reference states associated with the resources and condition limits bounding the reference states for the respective resource;
    managing, by the plurality of first controllers, the allocation of the plurality of resources to maintain the condition limits bounding the reference states for the respective resources so that the respective reference state does not exceed the corresponding condition limit for the respective resource;
    monitoring, by a second controller, the resources allocated by the plurality of first controllers with respect to completion of a process;
    predicting, by the second controller, a time of completion of the process by the resources; and
    providing, by the second controller, feedback to one or more of the plurality of first controllers when the predicted of time of completion exceeds an allotted time duration for the process, the respective one or more of the plurality of first controllers to adjust a configuration of at least one of the plurality of resources based on the feedback from the second controller.

16. The computer-readable storage device of claim 15, wherein the instructions, when executed, cause the computer to adjust, based on the feedback, the allocation of resources from a first resource lacking capacity to a second resource with available capacity.

17. The computer-readable storage device of claim 15, wherein the condition limits bounding the reference states for the resources include a capacity limit and a wait time threshold.

18. The computer-readable storage device of claim 17, wherein the condition limits trigger one or more of the plurality of first controllers to allocate resources to achieve a minimum wait state through an interval of time based on the feedback from the second controller.

19. The computer-readable storage device of claim 18, wherein the allocated resources are located in a plurality of departments of the healthcare facility.

20. The computer-readable storage device of claim 15, wherein the first controller is to resolve a computed operational plan defining the process against the reference states of the resources allocated to execute the process so that locations, duty cycles, and sequences of the resources are met within the condition limits and the allotted time duration for the process.

* * * * *